(12) United States Patent
Gangjee

(10) Patent No.: US 10,189,853 B2
(45) Date of Patent: *Jan. 29, 2019

US010189853B2

(54) CONFORMATIONALLY RESTRICTED 4-SUBSTITUTED-2,6-DIMETHYLFURO[2,3-D]PYRIMIDINES AS ANTI-TUMOR AGENTS

(71) Applicant: DUQUESNE UNIVERSITY OF THE HOLY SPIRIT, Pittsburgh, PA (US)

(72) Inventor: Aleem Gangjee, Allison Park, PA (US)

(73) Assignee: Duquesne University of the Holy Spirit, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/536,022

(22) PCT Filed: Dec. 16, 2015

(86) PCT No.: PCT/US2015/066062
§ 371 (c)(1),
(2) Date: Jun. 14, 2017

(87) PCT Pub. No.: WO2016/100495
PCT Pub. Date: Jun. 23, 2016

(65) Prior Publication Data
US 2017/0369500 A1    Dec. 28, 2017

Related U.S. Application Data

(60) Provisional application No. 62/093,147, filed on Dec. 17, 2014.

(51) Int. Cl.
*C07D 491/048* (2006.01)
*A61K 31/519* (2006.01)

(52) U.S. Cl.
CPC ........ *C07D 491/048* (2013.01); *A61K 31/519* (2013.01)

(58) Field of Classification Search
CPC .................... C07D 491/048; A61K 31/519
See application file for complete search history.

(56) References Cited

U.S. PATENT DOCUMENTS

| 9,777,012 | B2* | 10/2017 | Gangjee ............. C07D 491/048 |
| 2003/0225098 | A1 | 12/2003 | Hirst et al. |
| 2005/0256140 | A1 | 11/2005 | Luke et al. |
| 2010/0048591 | A1 | 2/2010 | Flynn et al. |
| 2012/0264768 | A1 | 10/2012 | Gangjee |

FOREIGN PATENT DOCUMENTS

WO    WO-2012106522 A2 *  8/2012    ........... C07D 487/04

OTHER PUBLICATIONS

Gangjee et al., Discovery of Antitubulin Agents with Antiangiogenic Activity as Single Entities with Multitarget Chemotheraphy Potential, ACS Med. Chem. Lett. 2014, vol. 5, pp. 480-484 (Published: Feb. 27, 2014); p. 481, Fig 1, compound 6: Table 1.

* cited by examiner

*Primary Examiner* — John M Mauro
(74) *Attorney, Agent, or Firm* — Buchanan Ingersoll & Rooney PC; Craig G. Cochenour, Esq.

(57) ABSTRACT

The present invention provides conformationally restricted 4-substituted 2,6-dimethylfuro[2,3-d]pyrimidine compounds and pharmaceutical compositions comprising these compounds. Preferably, the compounds exhibit dual inhibition of microtubule assembly and receptor tyrosine kinases. Methods of treating cancer comprising administering a therapeutically effective amount of at least one conformationally restricted 4-substituted 2,6-dimethylfuro[2,3-d]pyrimidine compound to a patient is disclosed.

3 Claims, 12 Drawing Sheets colchicine combretastatin A-4

|  | R₁ | R₂ | R₃ |
|---|---|---|---|
| vinblastine | CH₃ | OCH₃ | COCH₃ |
| vincristine | CHO | OCH₃ | COCH₃ |
| vindesine | CH₃ | NH₂ | H | vinorelbine

DAMA-Colchicine

TOC Graphic

Different energy minimized and docked conformations of the potent conformationally restricted dual tubulin and RTK inhibitor 10.

Alternate TOC Graphics

Compound 10 adpots conformations different from its energy minimum in its docked poses in tubulin and RTKs

CONFORMATIONALLY RESTRICTED 4-SUBSTITUTED-2,6-DIMETHYLFURO[2,3-D]PYRIMIDINES AS ANTI-TUMOR AGENTS

CROSS-REFERENCE TO RELATED APPLICATION

This utility patent application claims the benefit of priority to U.S. Provisional Patent Application Ser. No. 62/093,147, filed Dec. 17, 2014. The entire contents of U.S. Provisional Patent Application Ser. No. 62/093,147 are incorporated by reference into this utility patent application as if fully rewritten herein.

STATEMENT REGARDING FEDERALLY SPONSORED RESEARCH OR DEVELOPMENT

This invention was made with government support under Grant No. CA142868 awarded by the National Cancer Institute, and Grant No. P30 CA054174 awarded by the CTRC Cancer Center, and Grant No. NMR: CHE 0614785 awarded by the National Science Foundation for an equipment grant for NMR instrumentation. The government has certain rights in the invention.

BACKGROUND OF THE INVENTION

1. Field of the Invention

This invention relates to conformationally restricted 4-Substituted-2,6-dimethylfuro[2,3-d]pyrimidine compounds and pharmaceutical compositions comprising conformationally restricted 4-Substituted-2,6-dimethylfuro[2,3-d]pyrimidines and pharmaceutically acceptable salts, solvates, or hydrates thereof. Methods of using these compounds and pharmaceutical compositions as multi-targeted receptor tyrosine kinase and microtubule inhibitors and as antitumor agents are provided.

2. Brief Description of the Background Art

Angiogenesis is the "life blood" of tumors and without a new blood supply tumors cannot grow and metastasize.[1] During carcinogenesis an angiogenic switch occurs and several angiogenic growth factors stimulate their receptor tyrosine kinases (RTKs) to initiate multiple pro-angiogenic events.[2] A therapeutic strategy to inhibit these key angiogenic proteins or their RTKs was envisioned[3-5] and multiple inhibitors targeting EGFR, VEGF and/or PDGFR-□ among others are now used clinically. These RTKs are noted to have multi-kinase effects,[6] and this appears to be important for optimal activities. Antiangiogenic therapies have proven to be useful clinically in combination with other approaches, and new agents continue to be developed.[6] FIG. 1 shows the structures of examples of chemically diverse microtubule depolymerizing agents.

Tubulin binding agents remain some of the most successful cytotoxic cancer chemotherapeutic agents in clinical use (FIG. 1).[7] These drugs can be classified as microtubule stabilizers, which stimulate tubulin polymerization, or destabilizers that inhibit tubulin polymerization.[8,9] Drugs that destabilize microtubules were noted to bind to tubulin at two major binding sites, the vinca domain and the colchicine site.[7] The vinca alkaloids including vincristine, vinblastine, and vindesine (FIG. 1) bind competitively within the vinca site. These vinca alkaloids have utility in the treatment of both solid and liquid tumors and are used in cancer therapy in both adults and children.[7] Structurally diverse natural products and their analogs, including eribulin mesylate and maytansine (FIG. 1) displace the vincas in a noncompetitive manner and they were assumed to bind within the vinca domain and initiate allosteric effects.[8,9] Very recent studies by the Steinmtz laboratory now demonstrate that maytansine binds to a distinct microtubule depolymerizer site on β-tubulin that they have designated as the maytansine[10] site. Occupancy of this site inhibits tubulin polymerization by preventing the addition of new subunits at the plus ends of the microtubule, a mechanism different from vinca site agents.[10] These microtubule targeting agents have clinical utility, since a maytansine derivative is the payload in the antibody drug conjugate T-DM1 (ado-trastuzumab emtansine, Kadcyla®) and eribulin is used in the treatment of breast cancer. The colchicine site is a third non-overlapping microtubule destabilizer binding site on β-tubulin and is located at its interface with α-tubulin. While colchicine is too toxic for use in cancer therapy, a number of colchicine site agents have been evaluated for clinical activity, including 2-methoxyestradiol (2ME2), combretastatin A-4 phosphate (CA-4P) (fosbretastatin), the combretastin CA-1P prodrug (OXi4503) as well as other closely related compounds.[7,11,12] The interaction of colchicine site agents is intriguing in that some colchicine site agents, notably 2ME2, were developed based on antiangiogenic effects while others including CA-4P, have antivascular effects that initiate rapid destruction of the tumor vasculature. Thus, while these colchicine site agents inhibit tubulin polymerization and cause microtubule depolymerization in cells, there are other mechanistic differences that are not fully understood.

Multidrug resistance remains a major challenge in the curative treatment of cancer, and colchicine site agents have advantages over other microtubule targeting agents because most of them circumvent the P-glycoprotein (Pgp)- and □III tubulin-mediated resistance that have been implicated in limiting the clinical efficacy of other microtubule targeting agents.[7,13] In spite of this no colchicine site agents have yet achieved FDA approval for anticancer therapy. This site has excellent potential for new drug discovery.

Vascular endothelial growth factor receptor (VEGFR), platelet derived growth factor receptor (PDGFR), epidermal growth factor receptor (EGFR) and other RTKs are inhibited by small molecules that have considerable utility as targeted cancer chemotherapeutic agents (see FIG. 2, examples of selected RTK inhibitors).[14-20] It is well established in the literature that these RTK inhibitors are cytostatic.[14,18,19] Combination chemotherapy with RTK inhibitors as the antiangiogenic component along with cytotoxic clinically used conventional chemotherapeutic agents are in clinical trials.[15,17,20] The advantages of combination chemotherapy, particularly with RTK inhibitors, addresses pathway redundancy,[17] as well as tumor heterogeneity among other resistance mechanisms, and is beneficial when RTK inhibitors are combined with conventional cancer therapeutics.[15,17,20]

We sought to combine both RTK inhibitory activities along with cytotoxic activities in single molecules to afford combination chemotherapeutics via single agents.[21,22] In keeping with the principles of combination chemotherapy[22,23] such single entities would act simultaneously at two or more distinct targets and prevent or delay the emergence of resistance, avoid drug-drug interactions, circumvent pharmacokinetic problems and overlapping toxicities that plague combination chemotherapy with two or more separate agents.[23] The present invention discloses the structures, design, synthesis and biological activities of novel conformationally restricted bicyclic furo[2,3-d]pyrimidines, which possess potent activities against both tubulin and RTKs.

SUMMARY OF THE INVENTION

The present invention meets the above described need by providing bicyclic compounds having RTK inhibitory activity and anti-multidrug resistance activity.

In one embodiment of this invention, a compound of Formula I is provided:

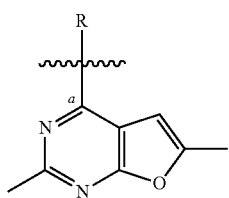

I wherein R is selected from the group consisting of:

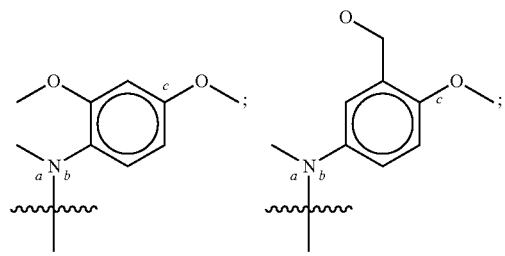

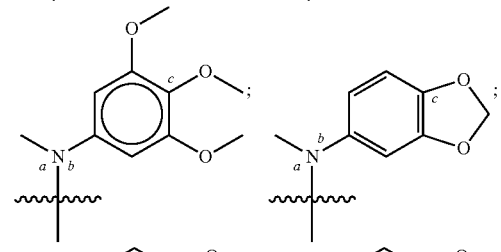

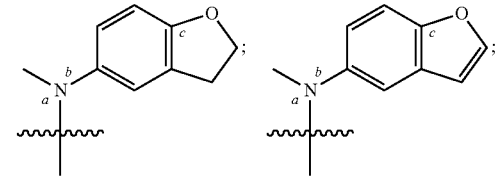

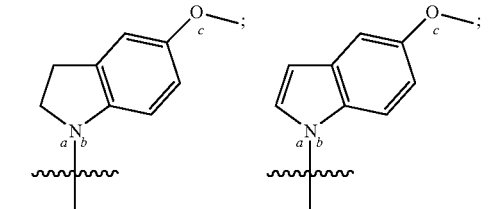

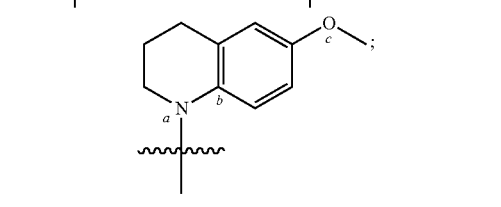

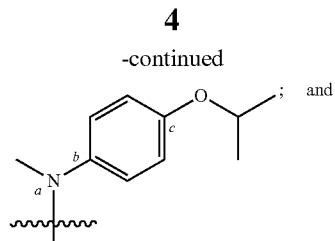

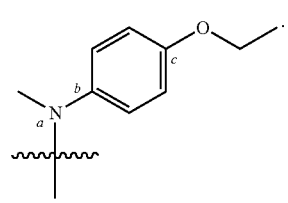

Another embodiment of this invention provides a pharmaceutical composition comprising a therapeutically effective amount of a composition of Formula I:

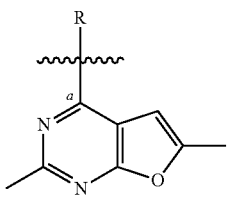

I wherein R is selected from the group consisting of:

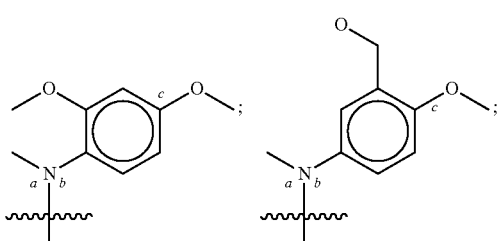

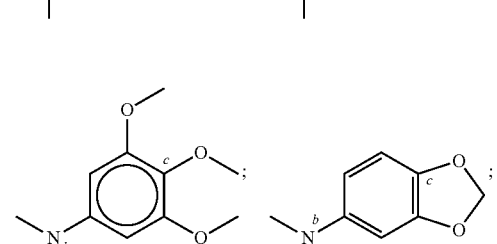

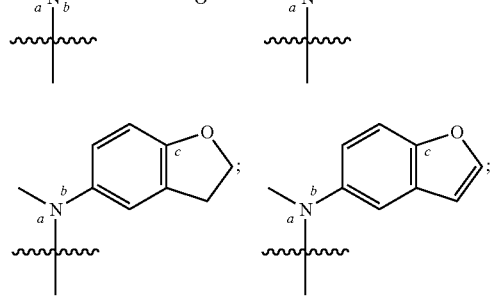

-continued

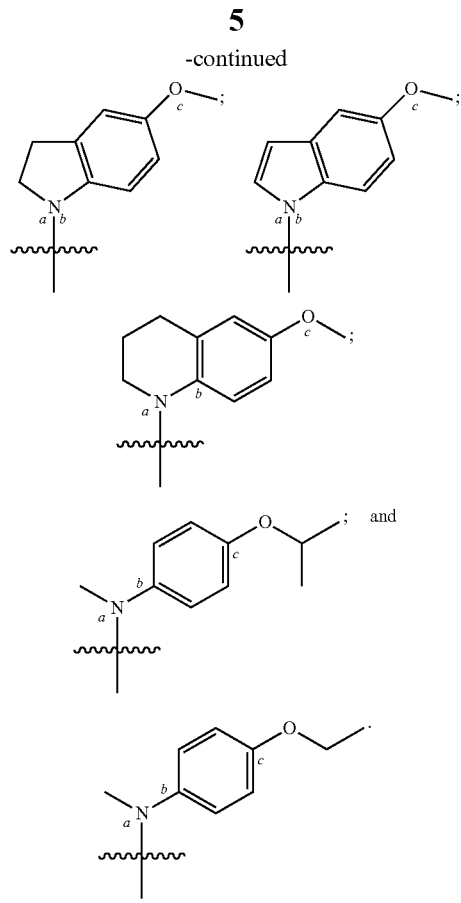

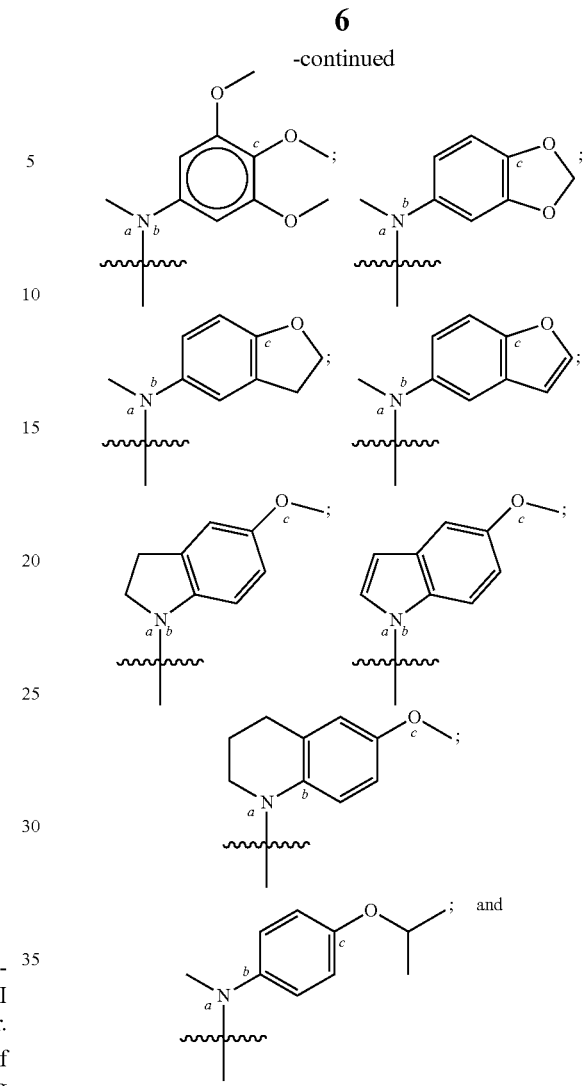

Another embodiment of this invention provides the hereinbefore disclosed pharmaceutical composition of Formula I comprising at least one pharmaceutically acceptable carrier.

In yet another embodiment of this invention, a method of treating a patient having a disease is provided comprising administering to a patient a therapeutically effective amount of at least one compound of Formula I:

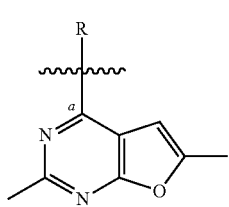

I wherein R is selected from the group consisting of:

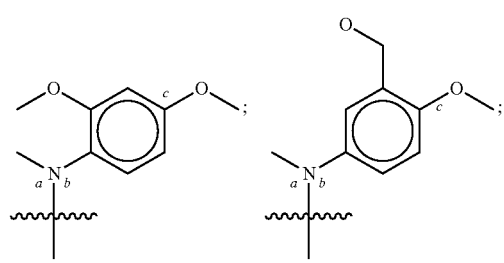

optionally comprising a pharmaceutically acceptable salt thereof. In a preferred embodiment of this invention, the method as disclosed hereinbefore is provided wherein the disease is cancer.

In another embodiment of this invention, a compound of Formula II is provided:

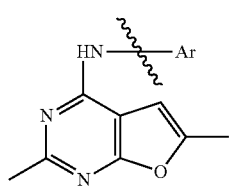

II wherein Ar is selected from the group consisting of:

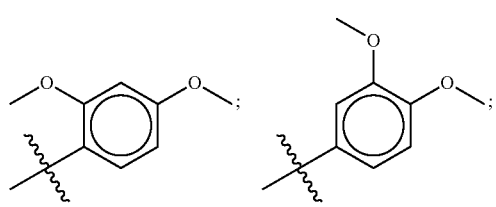

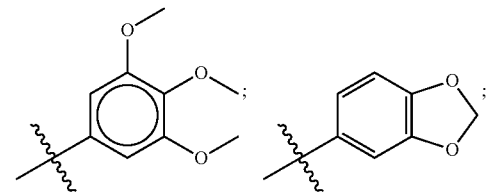

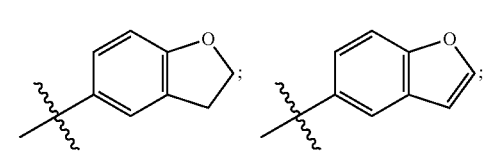

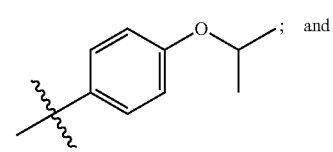

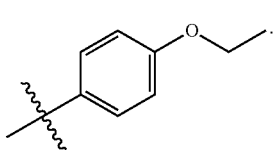

; and

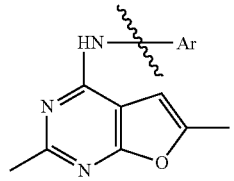

In another embodiment of this invention, a pharmaceutical composition comprising a therapeutically effective amount of a composition of Formula II is provided:

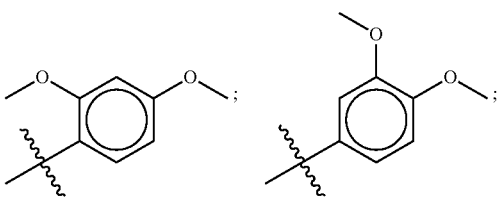

II wherein Ar is selected from the group consisting of:

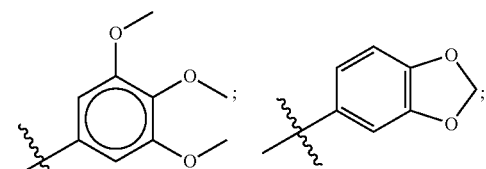

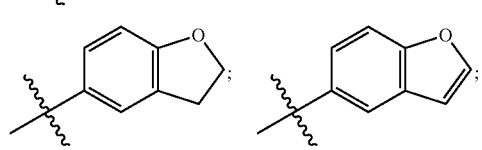

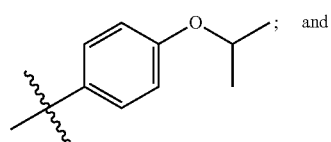

; and

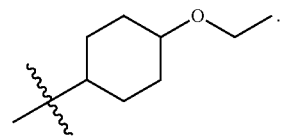

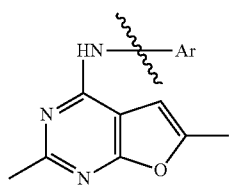

In yet another embodiment of this invention, the pharmaceutical composition set forth herein having the compound of Formula II, comprising at least one pharmaceutically acceptable carrier.

In another embodiment of this invention, a method is provided of treating a patient having a disease comprising administering to a patient a therapeutically effective amount of at least one compound of Formula II:

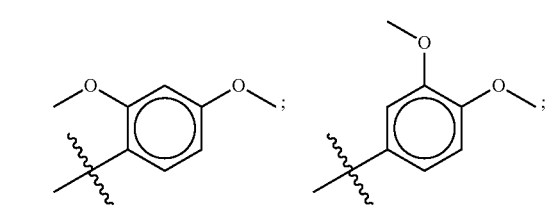

II wherein Ar is selected from the group consisting of:

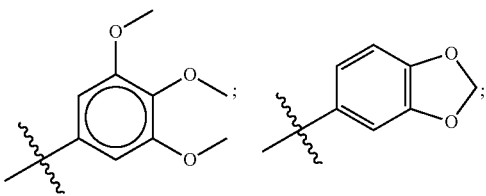

-continued

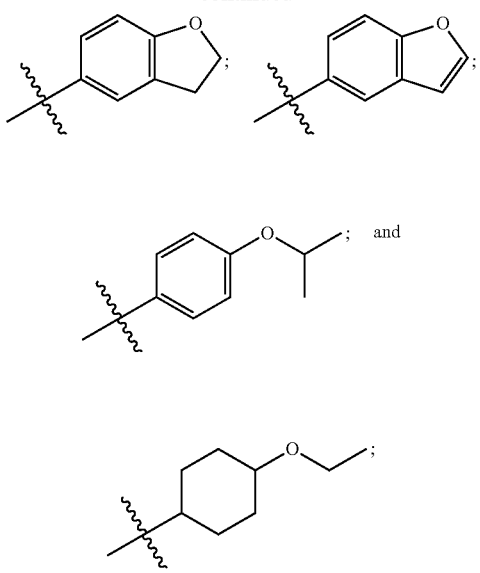

and optionally comprising a pharmaceutically acceptable salt thereof. Preferably, this method as disclosed herein includes wherein the disease is cancer.

Other embodiments of this invention provide the compounds having Formula I that are conformationally restricted.

In yet another embodiment, the pharmaceutical composition as disclosed herein comprises a pharmaceutically acceptable salt, solvate, or hydrate of the compound of Formula I. Preferably, the pharmaceutical composition having the compound of Formula I includes wherein the compound is conformationally restricted.

Other embodiments of this invention provide the compounds having Formula II that are conformationally restricted.

In yet another embodiment, the pharmaceutical composition as disclosed herein comprises a pharmaceutically acceptable salt, solvate, or hydrate of the compound of Formula II. Preferably, the pharmaceutical composition having the compound of Formula II includes wherein the compound is conformationally restricted.

Another embodiment of this invention provides a method of inhibiting multi-targeted receptor tyrosine kinases and/or microtubules comprising: administering to a patient a therapeutically effective amount of a compound of Formula I:

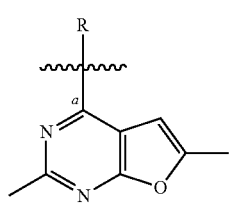

I wherein R is selected from the group consisting of:

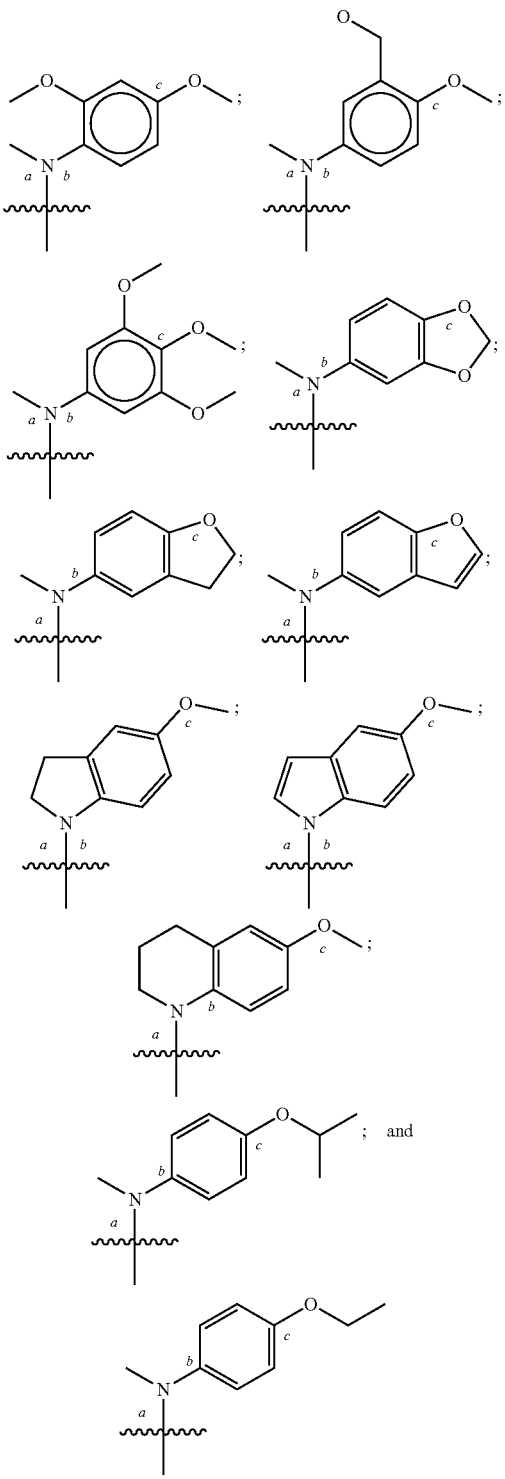

for inhibiting the receptor tyrosine kinases and/or the microtubules.

A method of inhibiting multi-targeted receptor tyrosine kinases and/or microtubules is provided comprising: administering to a patient a therapeutically effective amount of a compound of Formula II:

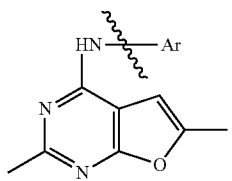

wherein Ar is selected from the group consisting of:

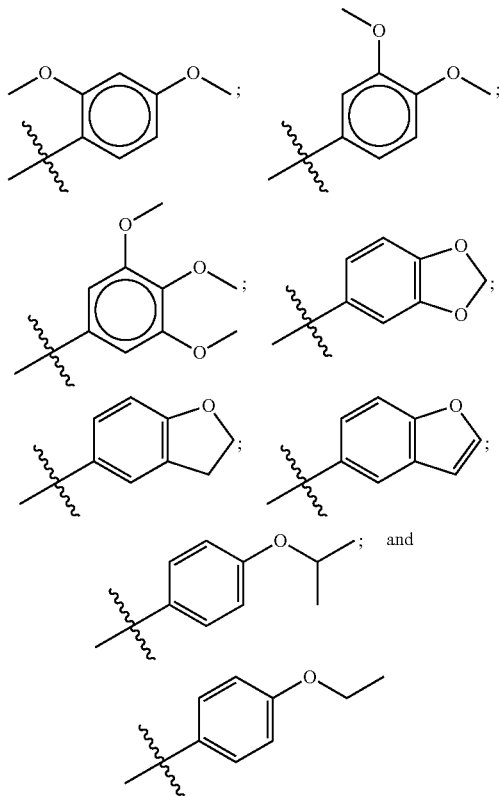

for inhibiting the receptor tyrosine kinases and/or the microtubules.

DETAILED DESCRIPTION OF THE INVENTION

Figure 1:
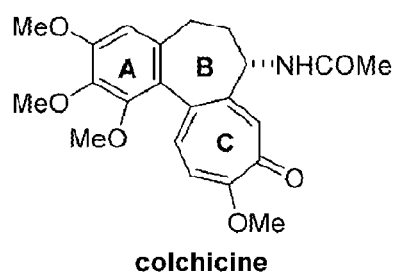
FIG. 1 shows structures of chemically diverse microtubule depolymerizing agents.
Figure 1:
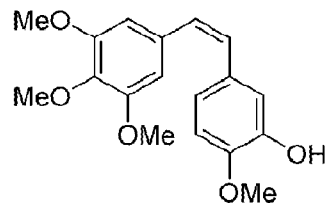
Figure 1:
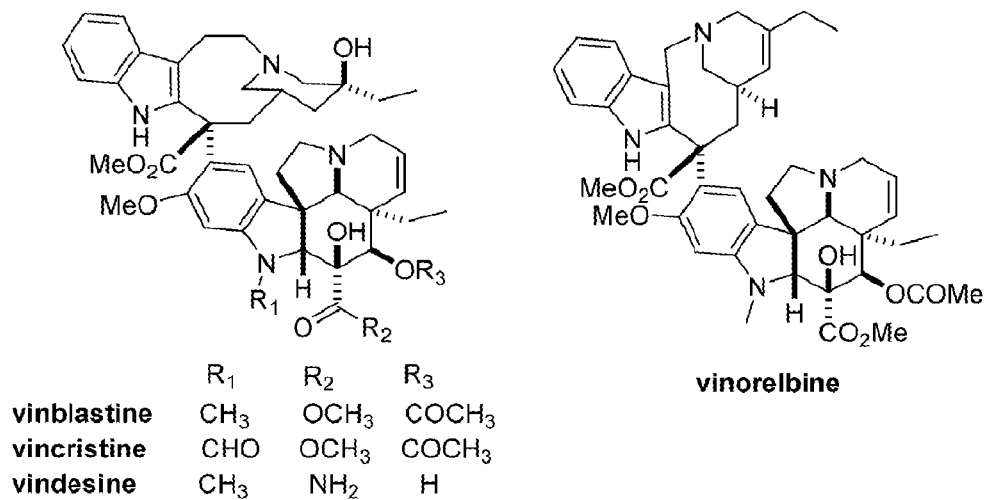

The present invention discloses the structure, design, synthesis and biological activities of novel conformationally restricted bicyclic furo[2,3-d]pyrimidine compounds and pharmaceutical compositions comprising these compounds and pharmaceutically acceptable salts, solvates, or hydrates thereof, which possess potent activities against both tubulin and RTKs.

As used herein, abbreviations are as follows: combretastatin A-4 (CA-4); vascular endothelial growth factor receptor-2 (VEGFR-2); receptor tyrosine kinases (RTKs); 2-methoxyestradiol (2ME2); platelet-derived growth factor receptor β (PDGFR-β); chorioallantoic membrane (CAM); and 2,3-Dichloro-5,6-dicyano-1,4-benzoquinone (DDQ).

As used herein, the term "patient" means members of the animal kingdom, including but not limited to, human beings.

As used herein, the term "having cancer" means that a patient has been diagnosed with cancer.

As used herein, the term "therapeutically effective amount" refers to that amount of any of the present compounds that is required to bring about a desired effect in a patient. The desired effect will vary depending on the illness being treated. For example, the desired effect may be reducing tumor size, destroying cancerous cells, and/or preventing metastasis, any one of which may be the desired therapeutically effective response. On its most basic level, a therapeutically effect amount is that amount needed to inhibit the mitosis of a cancerous cell or to facilitate the reversal of multidrug resistance. Any amount of mitotic inhibition or reversal of multidrug resistance will yield a benefit to a patient and is therefore within the scope of the invention.

In one embodiment of this invention, a compound of Formula I is provided:

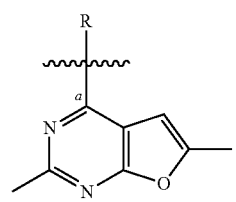

wherein R is selected from the group consisting of:
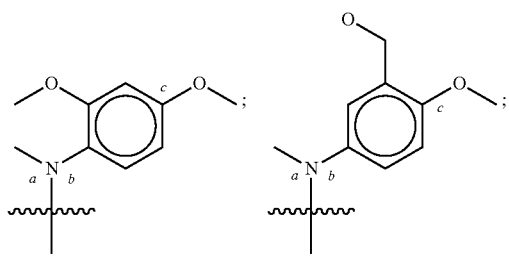
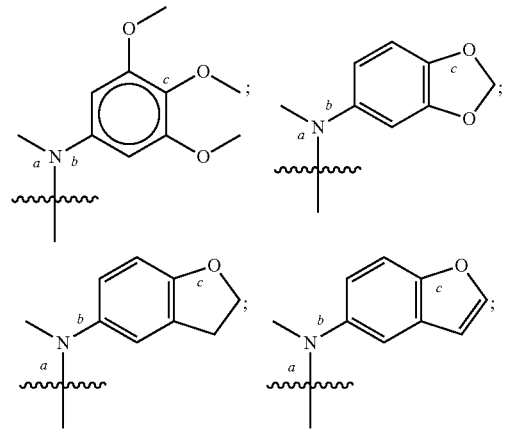
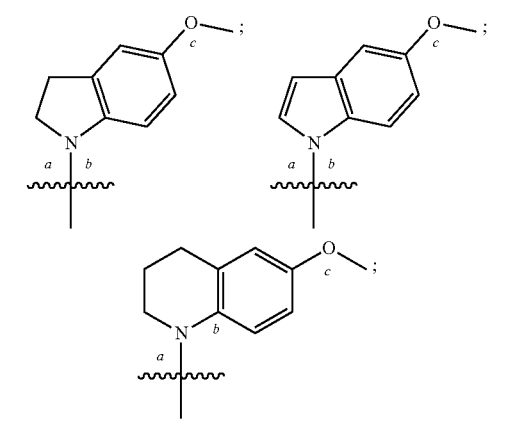
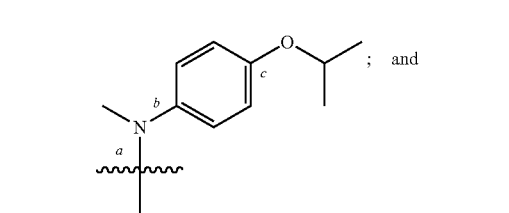
; and
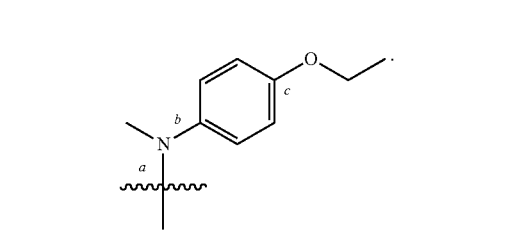
Another embodiment of this invention provides a pharmaceutical composition comprising a therapeutically effective amount of a composition of Formula I:
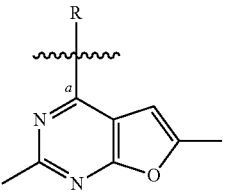
wherein R is selected from the group consisting of:
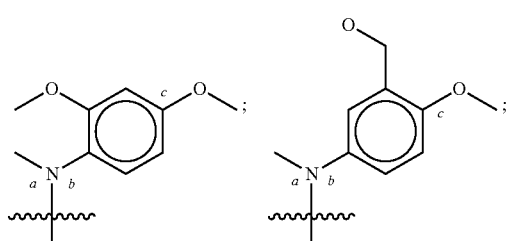
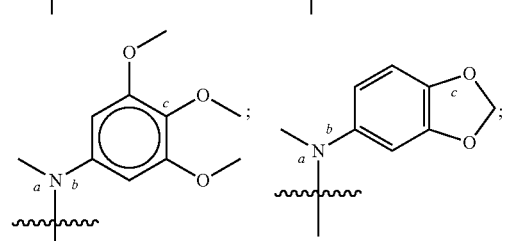
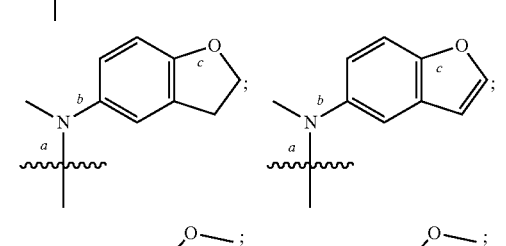
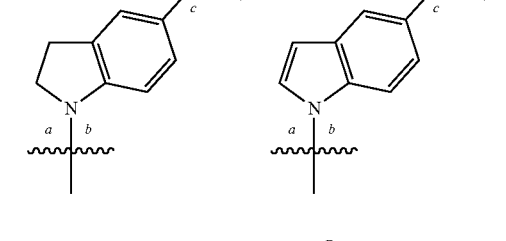
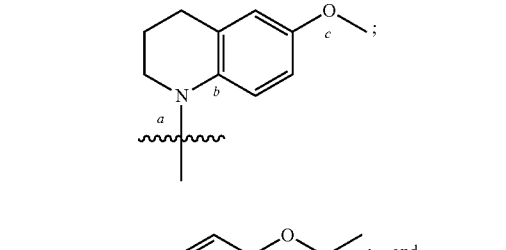
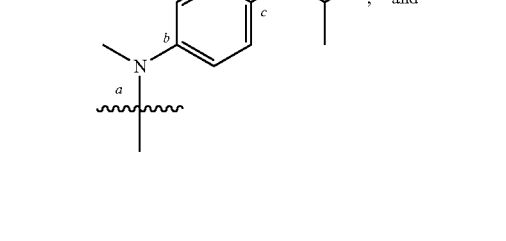
; and

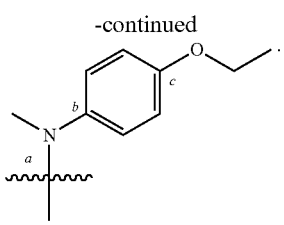

Another embodiment of this invention provides the hereinbefore disclosed pharmaceutical composition of Formula I comprising at least one pharmaceutically acceptable carrier.

In yet another embodiment of this invention, a method of treating a patient having a disease is provided comprising administering to a patient a therapeutically effective amount of at least one compound of Formula I:

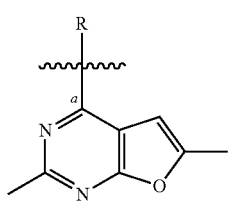

I wherein R is selected from the group consisting of:

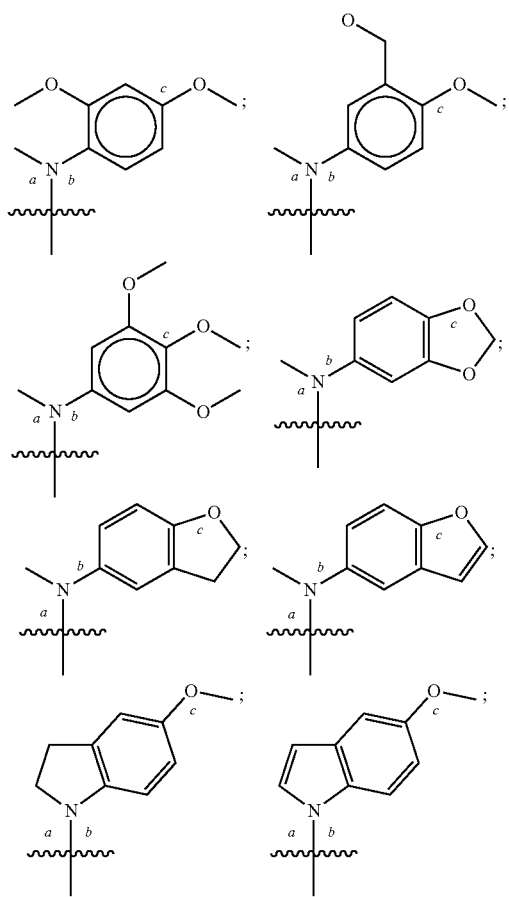

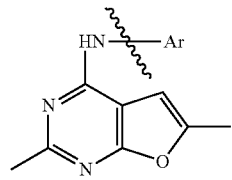

and optionally comprising a pharmaceutically acceptable salt thereof. In a preferred embodiment of this invention, the method as disclosed hereinbefore is provided wherein the disease is cancer.

In another embodiment of this invention, a compound of Formula II is provided:

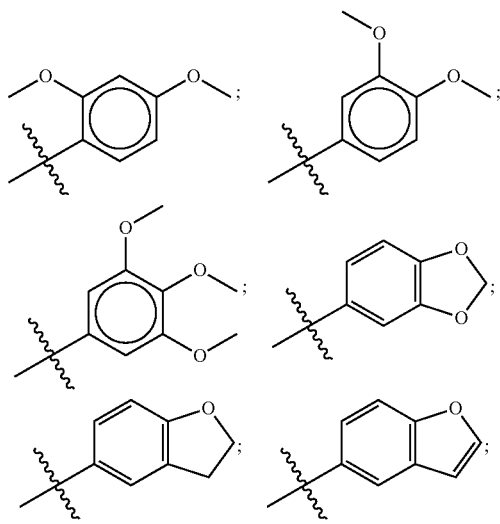

II wherein Ar is selected from the group consisting of:

17

-continued

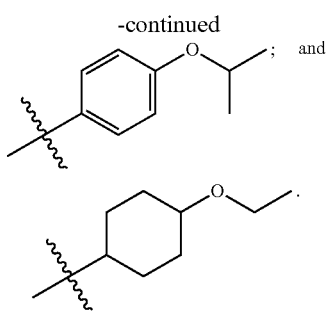; and

In another embodiment of this invention, a pharmaceutical composition comprising a therapeutically effective amount of a composition of Formula II is provided:

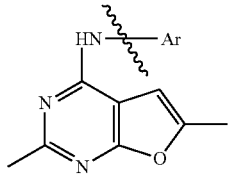

II wherein Ar is selected from the group consisting of:

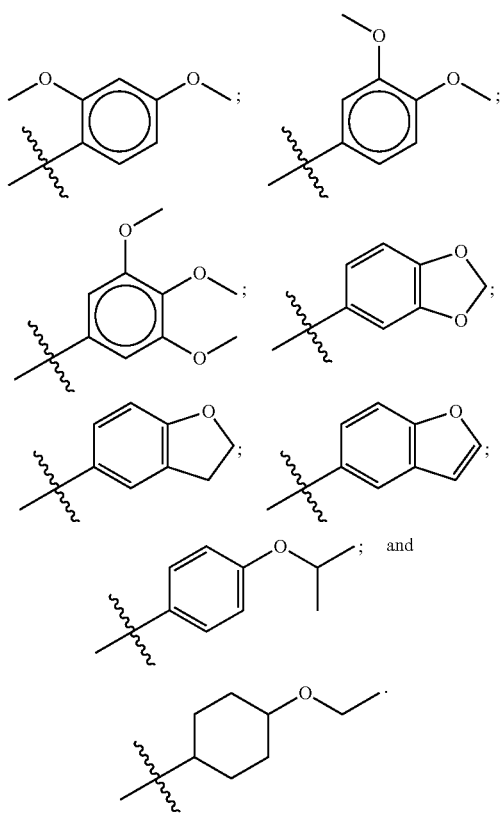

In yet another embodiment of this invention, the pharmaceutical composition set forth herein having the compound of Formula II, comprising at least one pharmaceutically acceptable carrier.

18

In another embodiment of this invention, a method is provided of treating a patient having a disease comprising administering to a patient a therapeutically effective amount of at least one compound of Formula II:

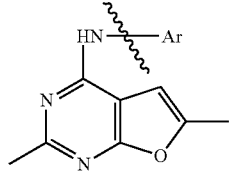

II wherein Ar is selected from the group consisting of:

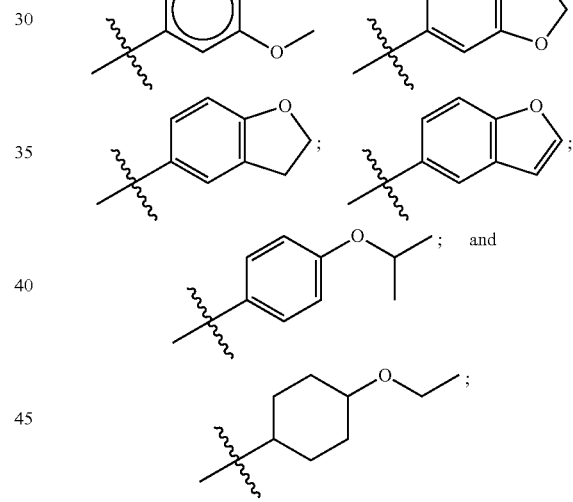

and optionally comprising a pharmaceutically acceptable salt thereof. Preferably, this method as disclosed herein includes wherein the disease is cancer.

Other embodiments of this invention provide the compounds having Formula I that are conformationally restricted.

In yet another embodiment, the pharmaceutical composition as disclosed herein comprises a pharmaceutically acceptable salt, solvate, or hydrate of the compound of Formula I. Preferably, the pharmaceutical composition having the compound of Formula I includes wherein the compound is conformationally restricted.

Other embodiments of this invention provide the compounds having Formula II that are conformationally restricted.

In yet another embodiment, the pharmaceutical composition as disclosed herein comprises a pharmaceutically acceptable salt, solvate, or hydrate of the compound of Formula II. Preferably, the pharmaceutical composition having the compound of Formula II includes wherein the compound is conformationally restricted.

Another embodiment of this invention provides a method of inhibiting multi-targeted receptor tyrosine kinases and/or microtubules comprising: administering to a patient a therapeutically effective amount of a compound of Formula I:

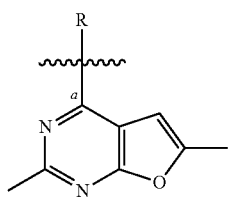

I wherein R is selected from the group consisting of:

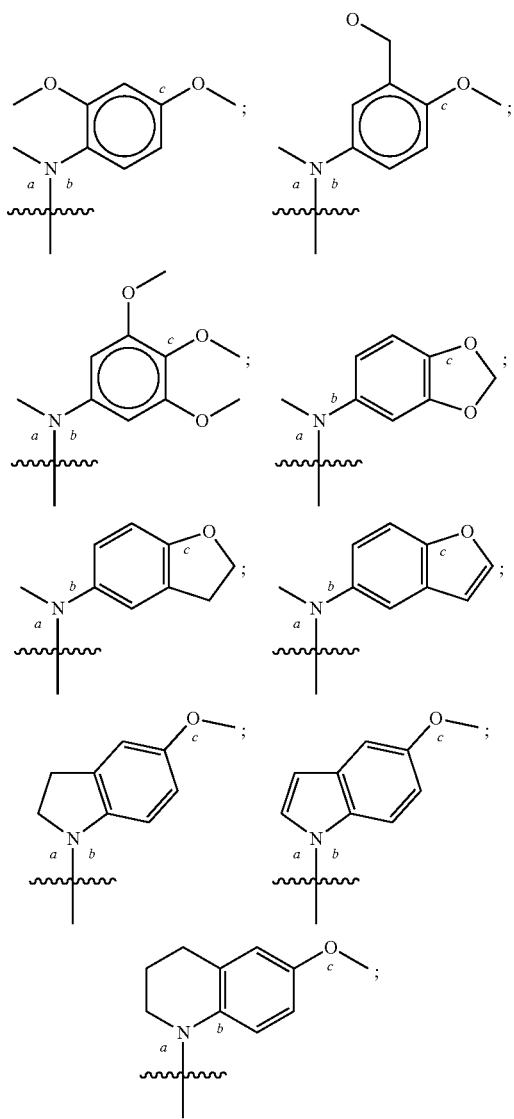

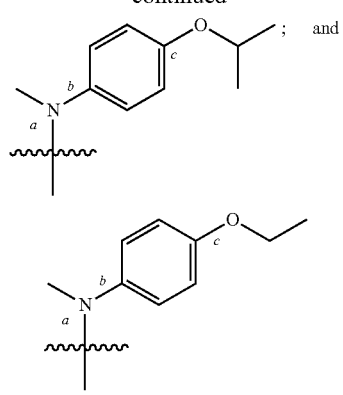

for inhibiting the receptor tyrosine kinases and/or the microtubules.

A method of inhibiting multi-targeted receptor tyrosine kinases and/or microtubules is provided comprising: administering to a patient a therapeutically effective amount of a compound of Formula II:

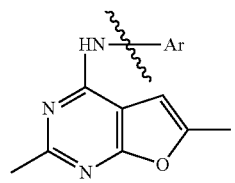

II wherein Ar is selected from the group consisting of:

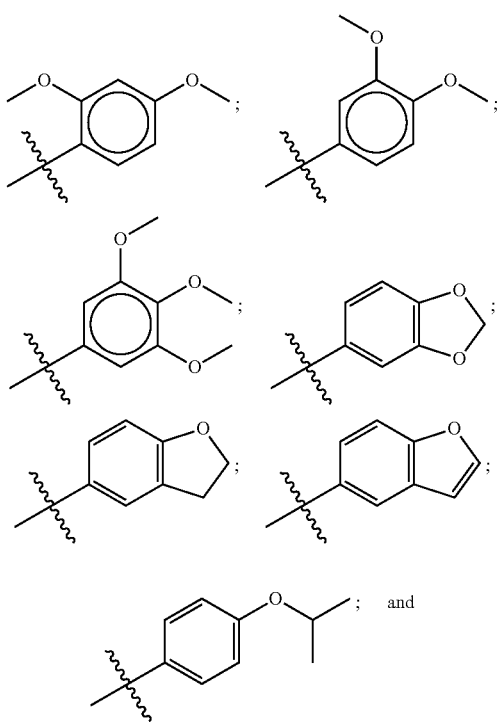

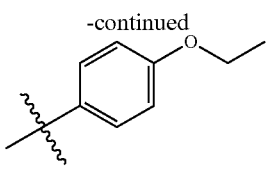

for inhibiting the receptor tyrosine kinases and/or the microtubules.

Figure 2:
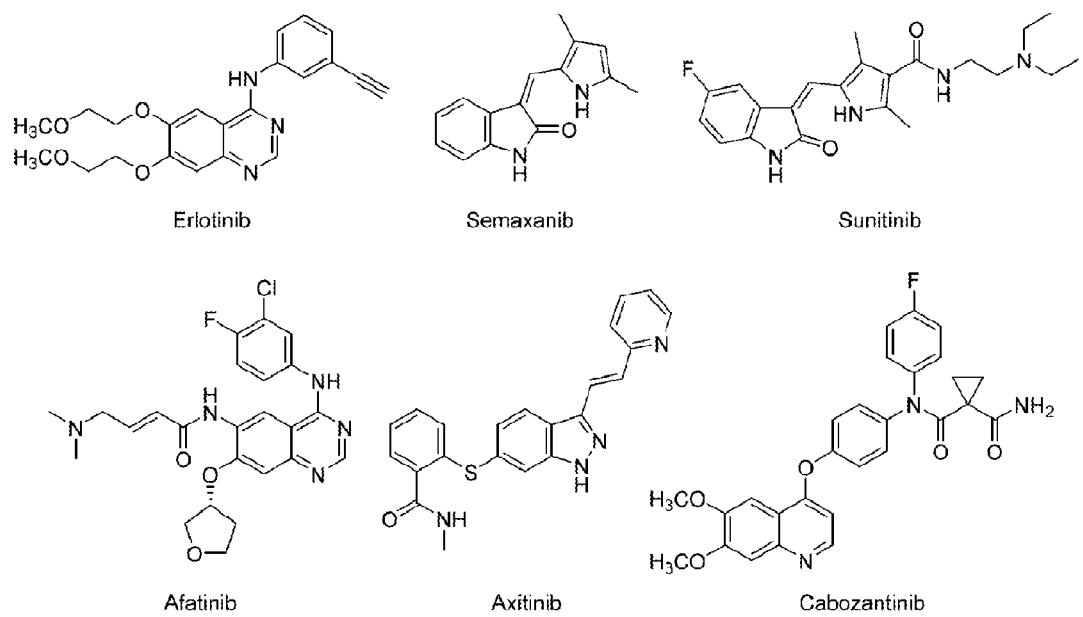
FIG. 2 shows the structures of selected RTK inhibitors.
Figure 3:
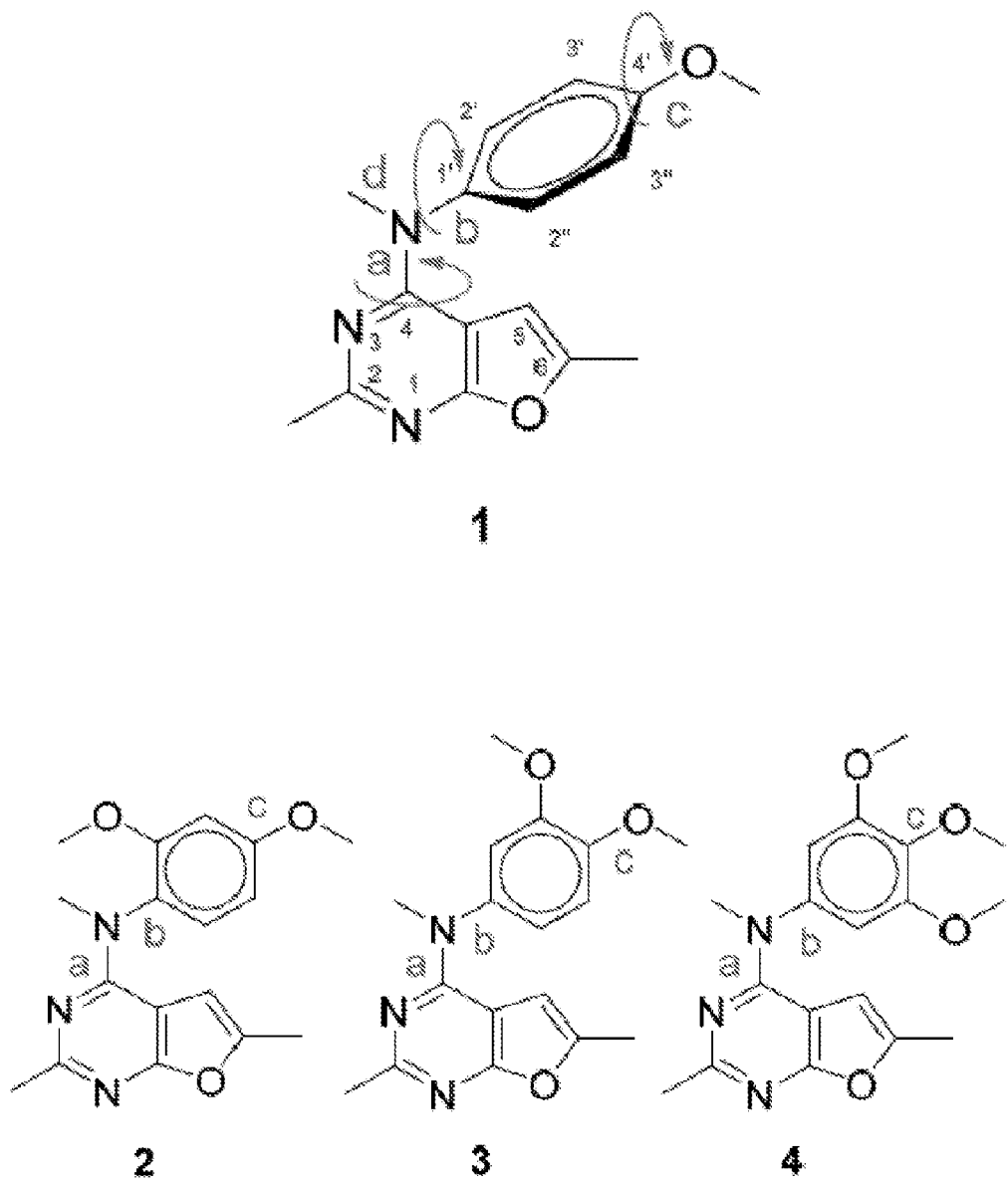
FIG. 3 shows the structures and conformational analysis of compounds 1-4.

The present inventor has recently reported the design and discovery of a series of novel bicyclic furo[2,3-d]pyrimidines[22], some of which possess both RTK and tubulin inhibitory properties and display potent in vivo antitumor activities. In this reported series of compounds, compound 1 (FIG. 3) showed the most potent activities against both RTKs and tubulin. As shown in FIG. 3, the bioactive conformation of compound 1 is determined by three rotatable single bonds: 4-position C—N bond (bond a), 1'-position C—N bond (bond b) and 4'-position C—O bond (bond c). Conformational analysis via molecular modeling and $^1$H NMR studies suggested that the methyl group on the aniline nitrogen in compound 1 restricted the free rotation of bond a as well as bond b (FIG. 2) and thus restricts the conformation of the anilino ring.[22] The potent activities of compound 1 against RTKs and tubulin were thought to be correlated with the conformational restriction in the molecule.[22]

To further explore the bioactive conformation and improve the biological activity of compound 1, compounds 2-4 (see, FIG. 3) of the present invention were designed, in which the free rotation of the bonds a, b and c were sequentially restricted. The initial strategy to explore the bioactive conformation was to increase the energy barrier for rotation by introducing bulky groups adjacent to the rotatable σ bonds. Thus, the energy barrier between the preferred conformation and non-preferred conformation is maximized, and the rotation of single bonds is restricted. In compounds 2-4 of the present invention, the methoxy group was chosen as the bulky moiety to replace the proton thus affording steric hindrance. Compound 1 (FIG. 3), which has a methoxy group at the 2'-position was designed to restrict the free rotation of bond b. Due to the steric clash between the 2'-methoxy group and N-methyl moiety, bond b is no longer freely rotatable. The 2'-methoxy group is three atoms away from bond a and meta to the 4'-methoxy group, thus the rotation of both bonds a and c are mostly unaffected. Compound 3 of the present invention (FIG. 3) was designed to restrict the free rotation of bond c. A methoxy group was introduced at the 3'-position, which is ortho to the 4'-methoxy group. Using molecular modeling we determined that compared to the 3'-proton in compound 1, the bulky 3'-methoxy group forces the methyl in the 4'-methoxy group to point away from the 3'-methoxy group. Compound 4 of the present invention (FIG. 3) was also designed to restrict the free rotation of bond c. Introduction of methoxy groups at both the 3' and 5'-positions, both of which are ortho to the 4'-position, severely restricts the rotation of bond c and forces the 4'-methoxy group to adopt a conformation that minimizes repulsive interactions with the ortho substitutions. Similar to compound 3, the rotation of bonds a and b are not affected in compound 4. We were aware that the additional methoxy groups in compounds 2-4 may not only restrict the free rotation of single bonds but also provide extra binding or hindrance to binding due to steric and/or electronic properties with the targets. The choice of the methoxy moieties was based on the molecular modeling docked poses of our previous analog compound 1 and its 4'-methoxy group overlap with the methoxy groups of colchicine in its binding pocket.

Figure 4:
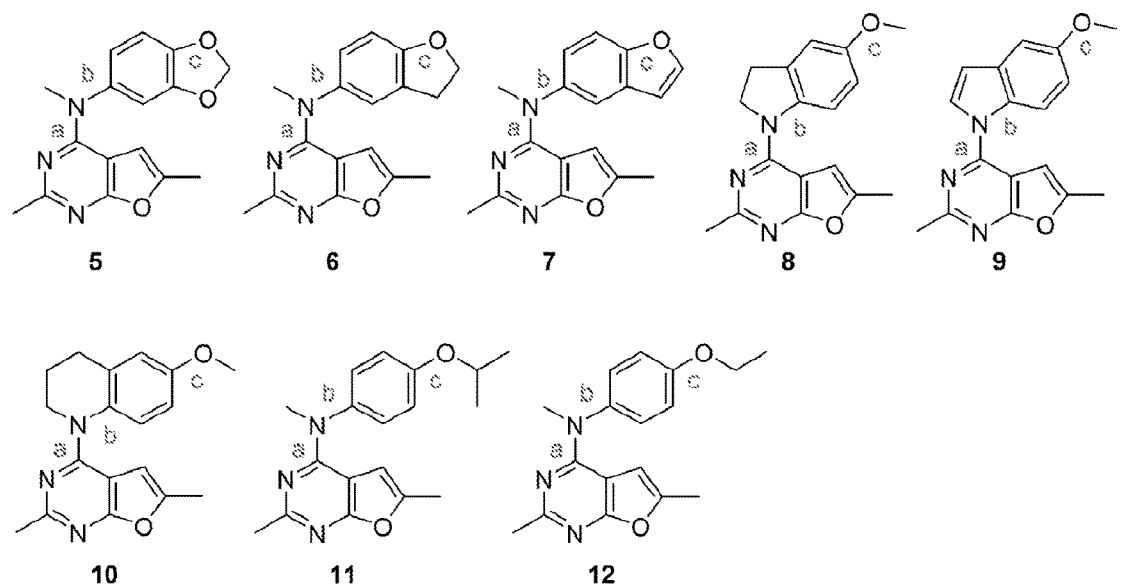
FIG. 4 shows the structures of compounds 5-12.

A second strategy to explore the influence of conformational restriction was to restrict the free rotation of single bonds by incorporating the bond into a ring. The single bonds in a ring are no longer freely rotatable. By changing the ring size and bond order, the conformation of the compounds can be further manipulated. With optimal ring size and bond order, the preferred conformation of the compound for activity could be defined. Compounds 5-10 of the present invention (FIG. 4) were designed using this strategy to explore the bioactive conformation.

In compounds 5-7 of the present invention, fused bicyclic systems were designed to replace the monocyclic 4'-methoxyphenyl group of compound 1. The 4'-methoxy group in compound 1 was converted to a methylenedioxy moiety as part of a fused bicyclic ring system. In compounds 5-7 of this invention, bond c is locked into a fixed conformation, while rotation of bonds a and b are mostly unaffected. The methylenedioxy ring in compound 5, the dihydrobenzofuran in compound 6, and the benzofuran in compound 7, mimic the function of the 4'-methoxy group in compound 1and could also provide additional binding interactions or steric hindrance with the target proteins.

Compounds 8-10 of the present invention were designed to restrict the rotation of bonds a and b with free rotation of bond c unaffected. In compound 8 of the present invention, the N-methyl moiety and the phenyl ring of compound 1 is connected through an additional carbon providing a dihydroindole ring. The N-methyl group and the phenyl ring in compound 1 were incorporated into an indole ring to give compound 9 of this invention. Connecting the N-methyl moiety and the phenyl ring via two carbon atoms affords the tetrahydroquinoline analog compound 10 of the present invention. Bond b in compounds 8-10 of the present invention is restricted by incorporation into a fused bicyclic ring system and is no longer freely rotatable. The bulk of the 4-N-substitutions also restrict the rotation of bond a in compounds 8-10 of the present invention. The dihydroindole of compound 8, the tetrahydroquinoline of compound 9, and indole analogs of compound 10 have different ring size and increased ring rigidity, thus the fused phenyl ring in compounds 8-10 was locked into somewhat different conformations, which may translate into increased potency and/or selectivity.

Compounds 11 and 12 of the present invention introduce bulk at the 4'-position of the aniline moiety and were designed to explore the effect of bulk at that position. In addition, the 4'-isopropyl of compound 11 and 4'-ethyl of compound 12 could also affect rotation around bond c.

A systematic conformational search around the rotatable bonds of compound 1 (bonds a, b and c, FIG. 3, 5° increments) and compound 10 (bonds a and c, FIG. 4) using Sybyl X 2.1.1[24] showed a dramatic reduction in the number of conformations for compound 10 (1525 conformations) compared to compound 1 (74,400 conformations), evidence of the expected conformational restriction due to the tetrahydroquinoline moiety. Similar reductions in the number of conformations were observed with the other restricted analogs (compounds 5-9, results not shown).

Proliferative diseases and/or disorders that may be treated according to the methods of the present invention include, without limitation, leukemia, non-small cell lung cancer, colon cancer, central nervous system (CNS) cancer, melanoma, ovarian cancer, renal cancer, prostate cancer, and breast cancer.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of a tricyclic compound of the present invention to produce the desired effect in association with a pharmaceutical carrier. The specification for the dosage unit forms of the invention are dictated by and directly dependent on the particular compound and the particular effect, or therapeutic response, that is desired to be achieved.

Compounds containing Formula I or Formula II, or pharmaceutically acceptable salts, prodrugs, solvates, or hydrates thereof, can be administered to a patient (an animal or human) via various routes including parenterally, orally or intraperitoneally. Parenteral administration includes the following routes that are outside the alimentary canal (digestive tract): intravenous; intramuscular; interstitial; intraarterial; subcutaneous; intraocular; intracranial; intraventricular; intrasynovial; transepithelial, including transdermal, pulmonary via inhalation, ophthalmic, sublingual and buccal; topical, including dermal, ocular, rectal, or nasal inhalation via insufflation or nebulization. Specific modes of administration shall depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered to a patient shall depend on the characteristics of the patient being treated, including for example, but not limited to, the patient's age, weight, health, and types and frequency of concurrent treatment, if any, of any other chemotherapeutic agent(s), all of which is determined by the clinician as one skilled in the art.

Compounds containing Formula I or Formula II, or a pharmaceutically acceptable salt, prodrug, solvate or hydrate thereof, that are orally administered can be enclosed in hard or soft shell gelatin capsules, or compressed into tablets. Compounds also can be incorporated with an excipient and used in the form of ingestible tablets, buccal tablets, troches, capsules, sachets, lozenges, elixirs, suspensions, syrups, wafers and the like. Compounds containing Formula II or Formula II can be in the form of a powder or granule, a solution or suspension in an aqueous liquid or non-aqueous liquid, or in an oil-in-water emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain the active compound, sucrose as a sweetening agent, methyl and propylparabens as preservatives, a dye and flavoring. Any material used in preparing any dosage unit form should be pharmaceutically pure and substantially non-toxic. Additionally, the compounds of Formula I or Formula II, or a pharmaceutically acceptable salt, prodrug, solvate or hydrate of the Formulae, can be incorporated into sustained-release preparations and formulations.

The compounds of Formula I or Formula II, or a pharmaceutically acceptable salt, prodrug, solvate or hydrate thereof, can be administered to the central nervous system, parenterally or intraperitoneally. Solutions of the compound as a free base or a pharmaceutically acceptable salt can be prepared in water mixed with a suitable surfactant, such as hydroxypropylcellulose. Dispersions also can be prepared in glycerol, liquid polyethylene glycols and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include, without limitation, sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi.

Compounds of the present invention may be contained within, mixed with, or associated with, a suitable (acceptable) pharmaceutical carrier for administration to a patient according to the particular route of administration desired. Suitable or acceptable pharmaceutical carriers refers to any pharmaceutical carrier that will solubilize the compounds of the present invention and that will not give rise to incompatability problems, and includes any and all solvents, dispersion media, coatings, antibacterial and antifungal agents, isotonic agents, absorption delaying agents, and the like. The use of such suitable or acceptable pharmaceutical carriers is well known by those skilled in the art. Preferred carriers include sterile water, physiologic saline, and five percent dextrose in water. Examples of other suitable or acceptable pharmaceutical carriers include, but are not limited to, ethanol, polyol (such as propylene glycol and liquid polyethylene glycol), suitable mixtures thereof, or vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the compound of Formula I or Formula II in the required amount in the appropriate solvent with various of the other ingredients enumerated above, as required, followed by filtered sterilization. Generally, dispersions are prepared by incorporating the sterilized compound of Formula I or Formula II into a sterile vehicle that contains the basic dispersion medium and any of the other ingredients from those enumerated above. In the case of sterile powders for the preparation of sterile injectable solutions, the preferred methods of preparation are vacuum drying and freeze drying.

Pharmaceutical compositions which are suitable for administration to the nose and buccal cavity include, without limitation, self-propelling and spray formulations, such as aerosol, atomizers and nebulizers.

The therapeutic compounds of Formula I and Formula II, as described herein, can be administered to a patient alone or in combination with pharmaceutically acceptable carriers or as pharmaceutically acceptable salts, solvates or hydrates thereof, the proportion of which is determined by the solubility and chemical nature of the compound, chosen route of administration to the patient and standard pharmaceutical practice.

The present invention is more particularly described in the following non-limiting examples, which are intended to be illustrative only, as numerous modifications and variations therein will be apparent to those skilled in the art.

Molecular Modeling

Figure 5:
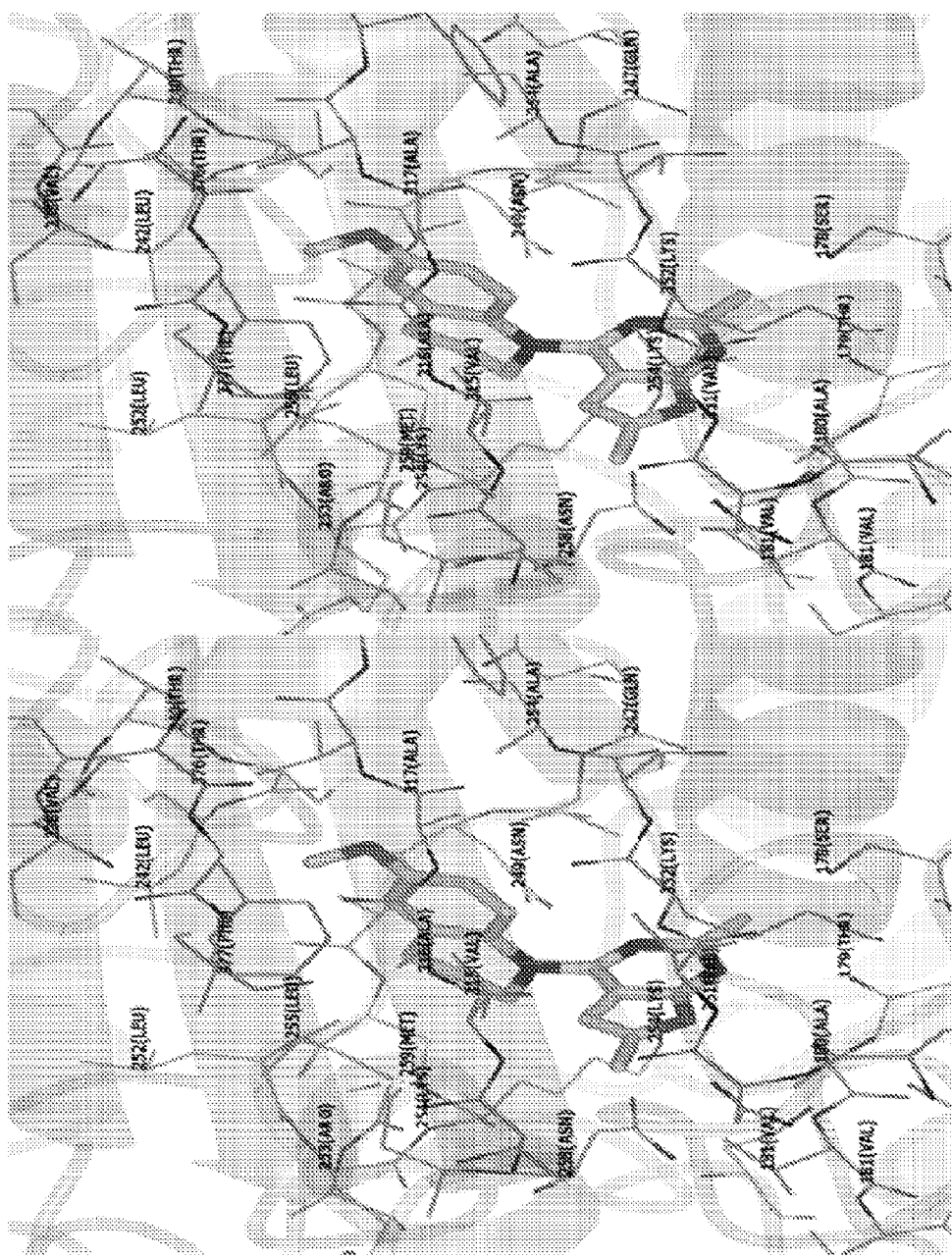
FIG. 5 shows a stereoview of a docked pose of compound 10 in the colchicine site of tubulin. PDB: 1SA0.[25]
Figure 5:
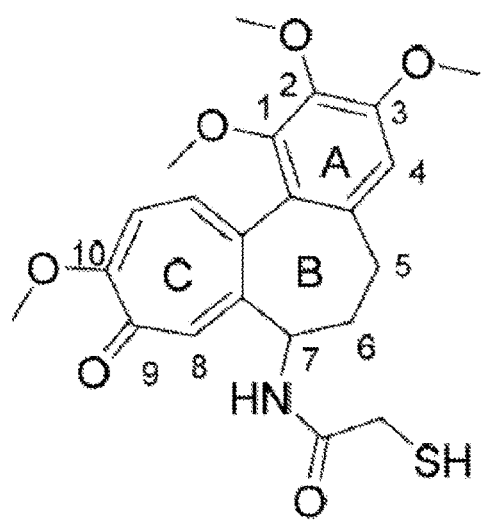

FIG. 5 shows a stereoview of a docked pose of compound 10 of this invention in the colchicine site of tubulin. PDB: 1SA0.[25]

Docking studies were performed for compounds 2-12 in the colchicine site of tubulin (PDB: 1SA0[25], 3.58 Å), VEGFR2 (PDB: 1YWN[26], 1.71 Å), EGFR (PDB: 1M17[27]) and in a homology model of PDGFR-β[21] using LeadIT 2.1.6[28] (validated by re-docking the crystal structure ligands) using previously reported methods.[21, 22] Docking studies of the lead compound 1[22] and standard compounds (semaxanib for VEGFR2, erlotinib for EGFR and sunitinib for PDGFR-β) were performed using the previous methods. The docked poses were visualized using the software CCP4 mg.[29]

Multiple low-energy conformations (within 1 kcal/mol of the best pose) were obtained on docking compounds 2-12 in the ATP site of the three target kinases and the colchicine site of tubulin. The docked conformation of compound 10 in the colchicine site of tubulin (FIG. 5) is presented as a working model for compounds 2-12 based on their similarity to the bound conformation of DAMA-colchicine[26] (FIG. 5, not shown in the model). The 6'-OMe phenyl group of compound 10 is oriented towards the triOMe containing A-ring of DAMA-colchicine and interacts with Leuβ246, Alaβ248, Leuβ253, Alaβ314, Ileβ376 and Valβ316. The 4'-OMe of compound 10 forms a hydrogen bond with Cysβ241, analogous to the hydrogen bond formed by the 3'-OMe group of DAMA-colchicine with Cysβ241. The tetrahydroquinoline ring of compound 10 occupies a region in space in proximity to the C5 and C6 of the B-ring of colchicine and is involved in hydrophobic interactions with Lysβ252, Alaβ248 and Leuβ246. The furo[2,3-d]pyrimidine scaffold of compound 10 partly overlaps with the C-ring of DAMA colchicine and forms hydrophobic interactions with Leuβ253, Asnβ256 and Lysβ250. Compound 10 had a docked score of −25.39 kJ/mol, which was better than the docked score of compound 1 (−23.41 kJ/mol). These results are in accord with results from recently published molecular modeling studies at the colchicine site of tubulin of compound 1.[22]

Figure 6:
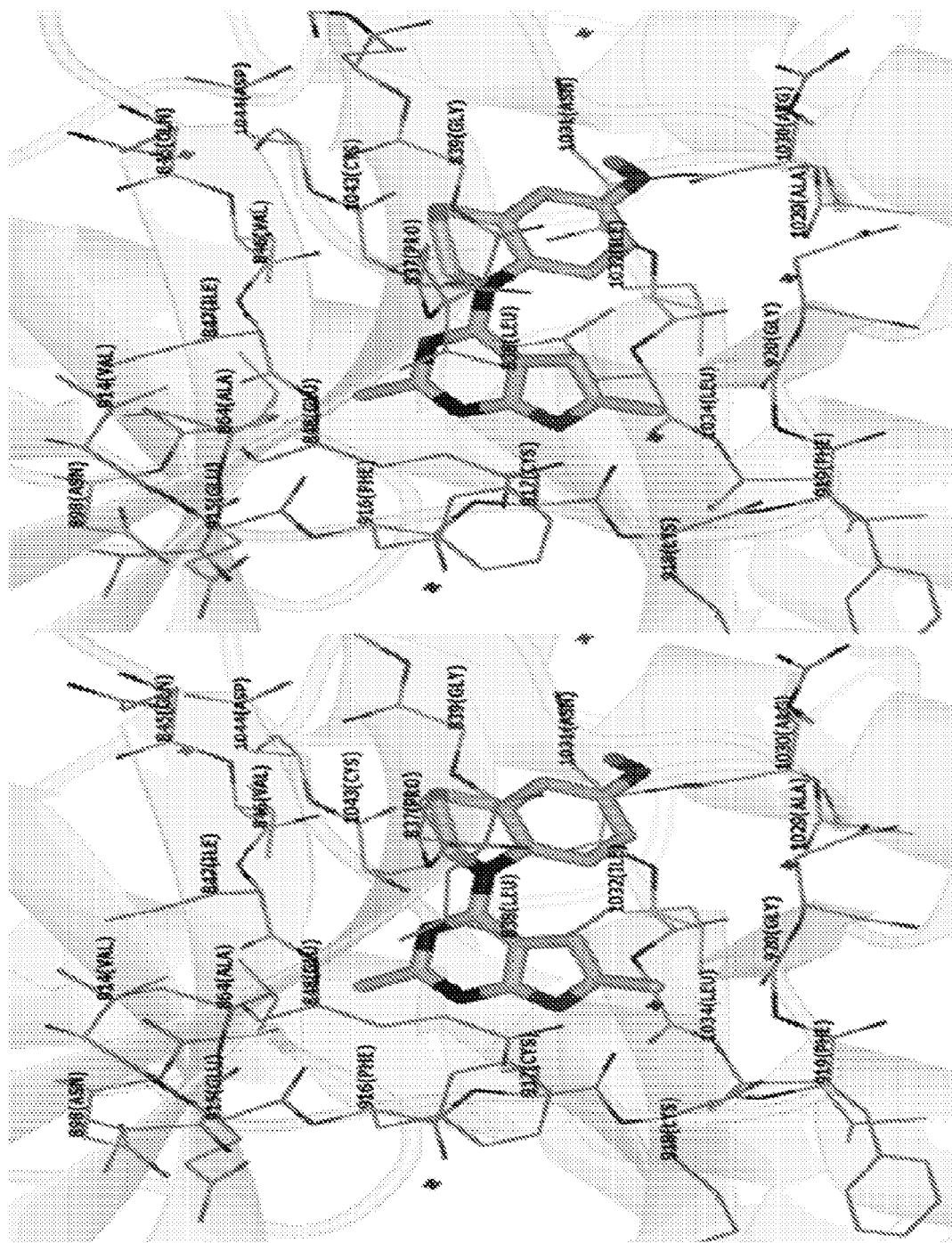
FIG. 6 shows a stereoview of a docked pose of compound 10 in VEGFR2. PDB: 1YWN[26]

FIG. 6 shows a stereo view of the docked pose of compound 10 in the ATP site of VEGFR2 (PDB: 1YWN[26]). The furo[2,3-d]pyrimidine scaffold of compound 10 is oriented parallel to the Hinge region amino acids and occupies the adenine binding region of the ATP site of VEGFR2. The N1 nitrogen of compound 10 forms a hydrogen bond with the backbone NH of Cys917 in the Hinge region. Additionally, the scaffold is stabilized by hydrophobic interactions with Leu838 and Leu1033. The bulk of the tetrahydroquinoline moiety forces a vertical orientation of the molecule in the pocket and additionally interacts with the side chain carbon atoms of Ile1042 and Cys1043. This vertical conformation orients the 6'-OMe moiety towards the Sugar binding pocket in the ATP site of VEGFR2.[26] The vertical orientation of the furo[2,3-d]pyrimidine scaffold of compound 10 is in contrast to the horizontal orientation of the purine ring of ATP in the ATP site of VEGFR2.[22, 30] Compound 10 showed an improved docking score of −24.98 kJ/mol compared to 1 (−23.78 kJ/mol) in VEGFR2.

Figure 7:
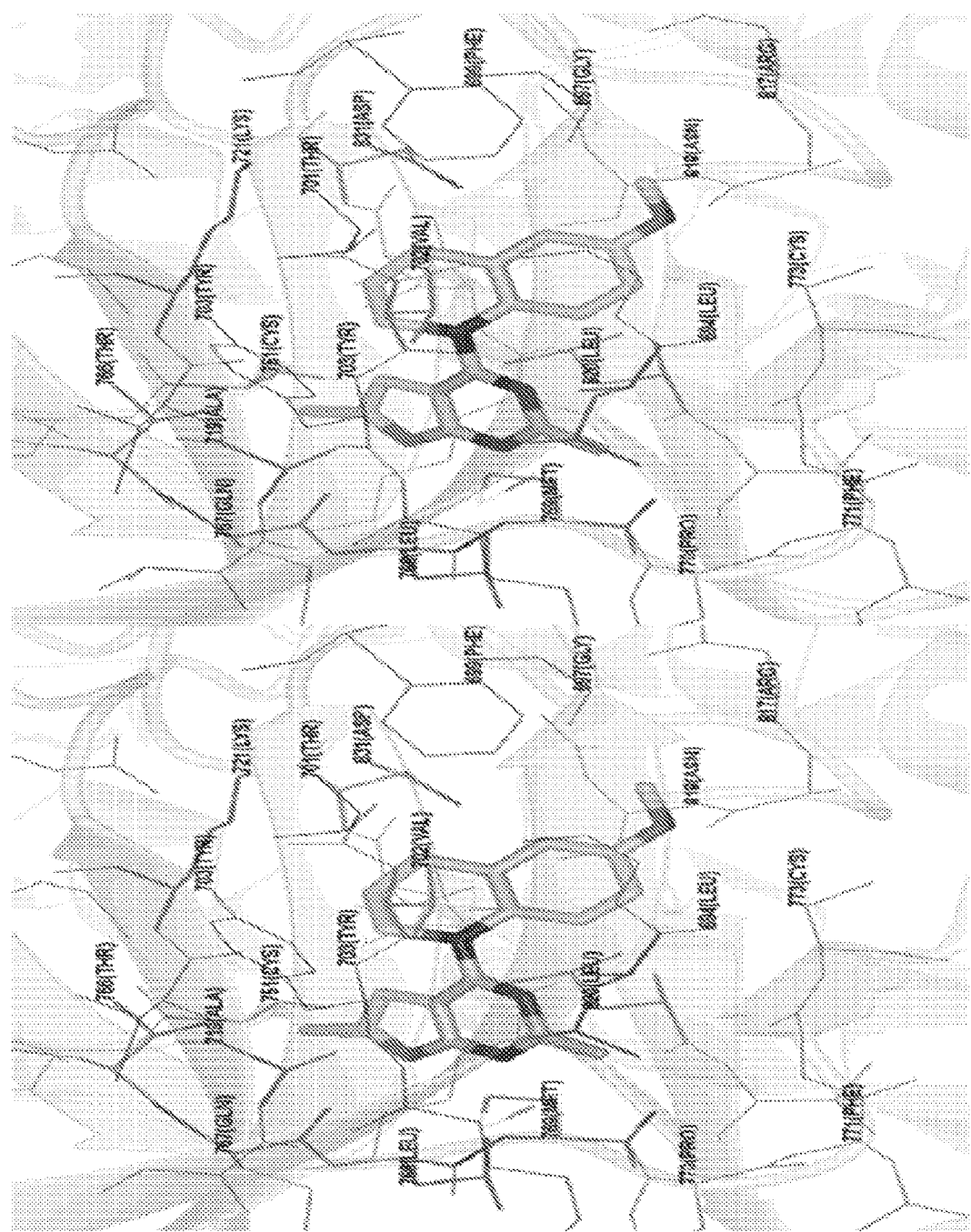
FIG. 7 shows a stereoview of a docked pose of compound 10 in EGFR. PDB: 1M17[27]

FIG. 7 shows the docked pose of compound 10 in the ATP site of EGFR (PDB: 1M17[27]). As with the docked pose of compound 10 in VEGFR2, the furo[2,3-d]pyrimidine scaffold of compound 10 is oriented parallel to the Hinge region due to the bulky tetrahydroquinoline ring and lies in the adenine binding region of the ATP binding site. The N1 nitrogen of compound 10 forms a hydrogen bond with the backbone NH of Met769 in the Hinge region. Additionally, the bicyclic scaffold forms hydrophobic interactions with Leu694, Met769, Leu820 and Met769. The 2-Me moiety interacts with Leu694 and Leu768 while the 6-Me moiety interacts with Cys751, Thr766, Leu768 and Met769. The tetrahydroquinoline moiety provides hydrophobic interactions with Phe699, Val702 and Lys721. In this conformation the 6'-OMe moiety lies in a polar pocket formed by the salt bridge between the side chains of Lys721 and Asp831. The vertical orientation of compound 10 is similar to that seen with the docked pose of compound 10 in VEGFR2 (FIG. 6) and is a consequence of the steric hindrance afforded by the tetrahydroquinoline with the Hinge region amino acids. The docked score of compound 10 was −26.16 kJ/mol, better than the docking score of −24.28 kJ/mol for compound 1 in these studies.

Figure 8:
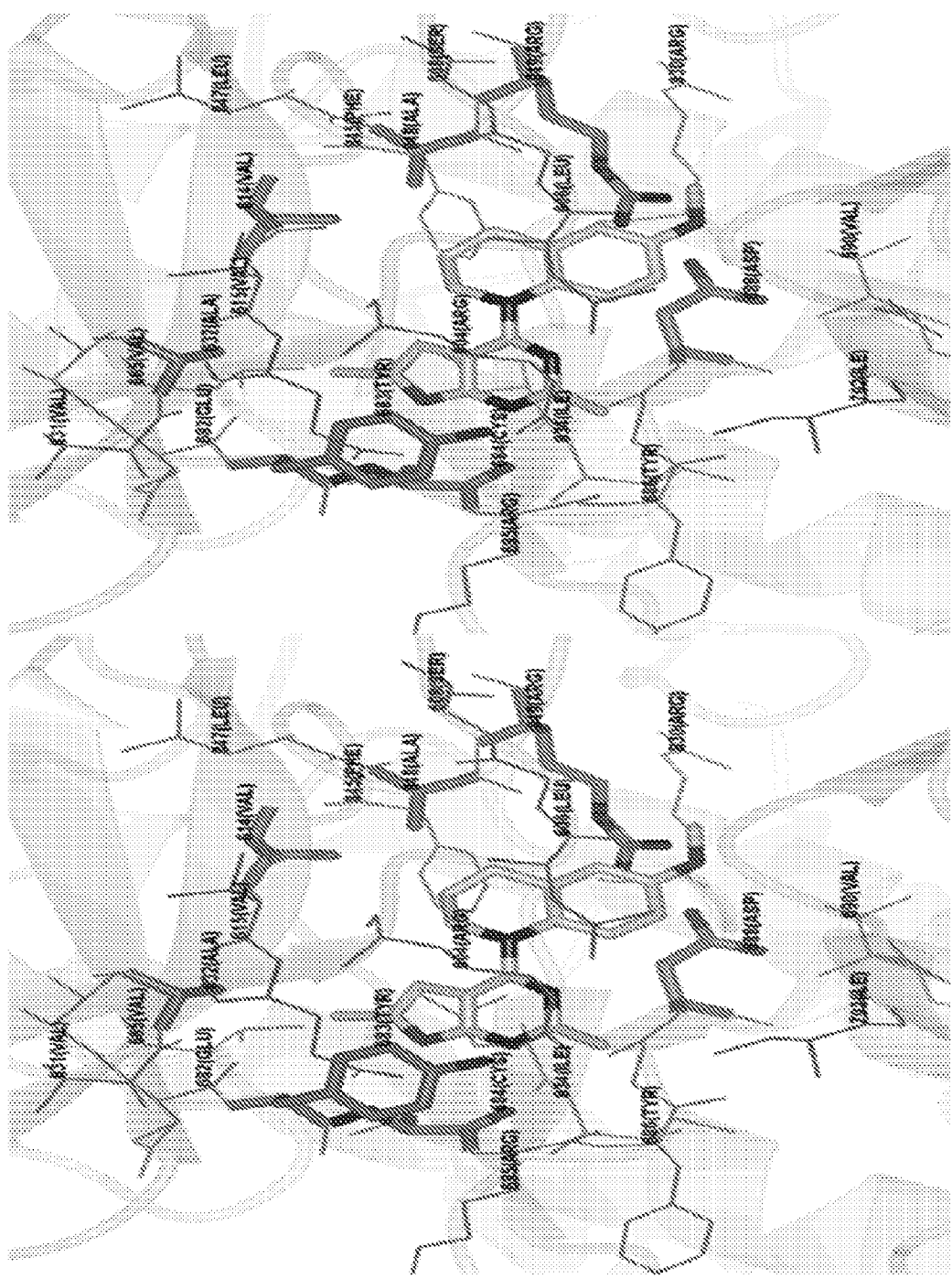
FIG. 8 shows a stereoview of a docked pose of compound 10 in a PDGFR-☐ homology model.[21]

FIG. 8 shows the docked pose of compound 10 in the ATP binding site of a PDGFR-β homology model.[21] The furo[2,3-d]pyrimidine scaffold of compound 10 is once again oriented parallel to the Hinge region and occupies the adenine region of the ATP site. The furo oxygen of compound 10 forms a hydrogen bond with the backbone NH of Cys684 in the Hinge region. The bicyclic scaffold forms hydrophobic interactions with Tyr683, Tyr686, Gly687 and Leu833 in the binding pocket. The 2-Me moiety interacts with Gly687 while the 6-Me moiety interacts with Ala632, Tyr683 and Leu833. The tetrahydroquinoline group interacts with Leu606 (not labeled), Val614 and Ala848. As is seen with the docked conformation of compound 10 in EGFR (FIG. 7), the 6'-OMe moiety lies in a polar pocket formed by the salt bridge formed between the side chains of Arg849 and Asp688. The docked score of compound 10 was −20.26 kJ/mol, better than the docked score of −19.01 kJ/mol for compound 1 in these studies.

Figure 9:
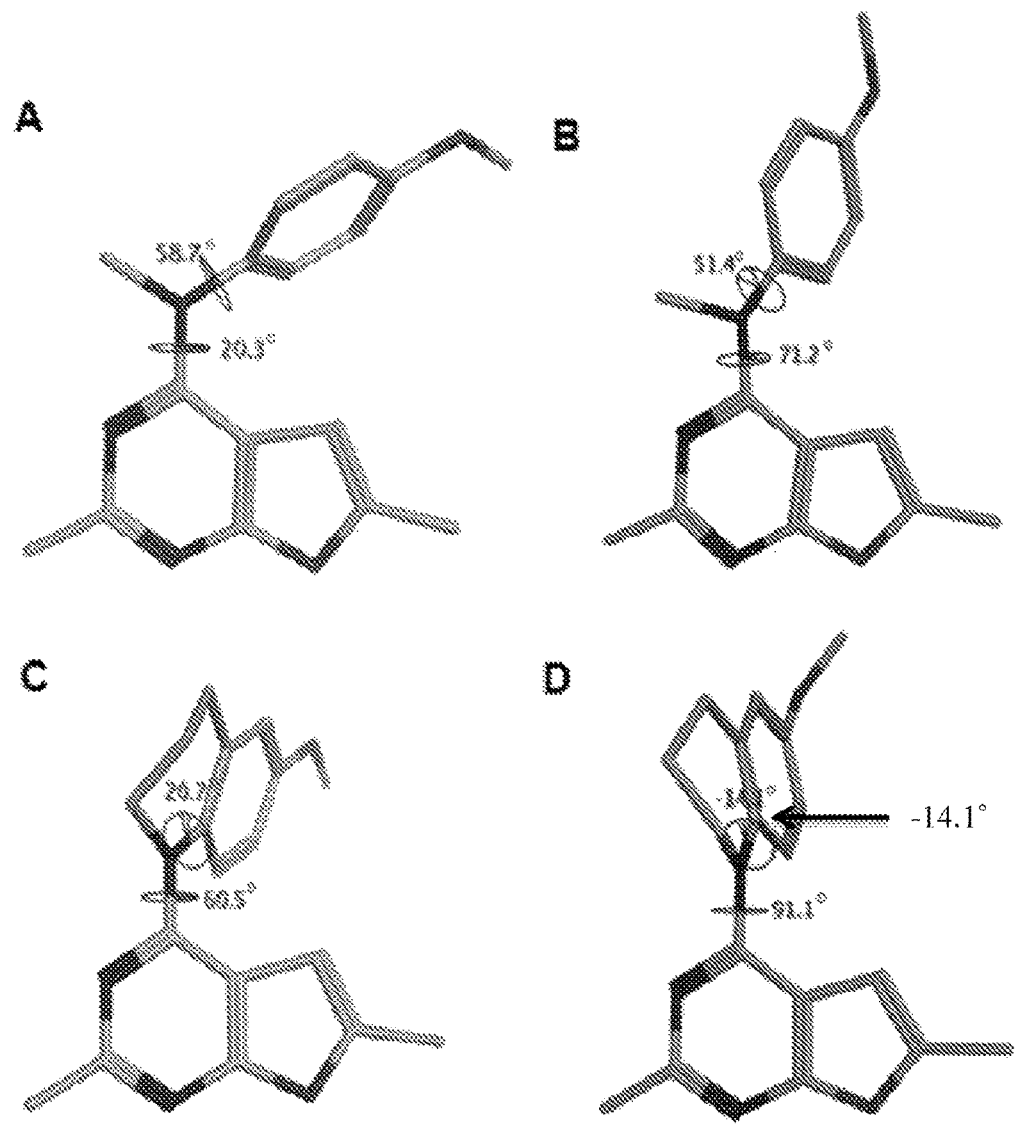
FIG. 9 shows a comparison of compound 1and compound 10 in the colchicine site of tubulin. Lowest energy conformations of compound 1(A) and compound 10 (C) predicted by the systematic conformational search. Docked conformations of compound 1 (B) and compound 10 (D) in the colchicine binding site of tubulin.

FIG. 9 shows a comparison of compound 1 and compound 10 in the colchicine site of tubulin. FIG. 9 shows the lowest energy conformations of compound 1 (A) and compound 10 (C) predicted by the systematic conformational search. Docked conformations of compound 1(B) and compound 10 (D) in the colchicine binding site of tubulin. The poses were generated by superimposition of the furo[2,3-d]pyrimidine scaffolds of the docked and energy minimum poses and highlight differences in the orientations of the 4-position substituents.

The conformations and energies of compound 1 and compound 10 in their lowest energy (FIGS. 9 A and C respectively) and the docked conformations in the colchicine site of tubulin (FIGS. 9 B and D respectively) are presented as representative examples of compounds 2-12. Analysis of these conformations indicates that the docked conformation of compound 10 is energetically (ΔE between conformations C and D in FIG. 9 is 0.42 kcal/mol) and conformationally closer to its lowest energy conformation compared to compound 1 (ΔE between conformations A and B in FIG. 9 is 3.7 kcal/mol). Thus, compound 10 could be anticipated to bind more efficiently to the colchicine site of tubulin compared to compound 1 and was expected to exhibit increased potency. Similar results were predicted for the other conformationally restricted analogs compounds 2-9 of this invention compared to compound 1 (modeling not shown).

Figure 10:
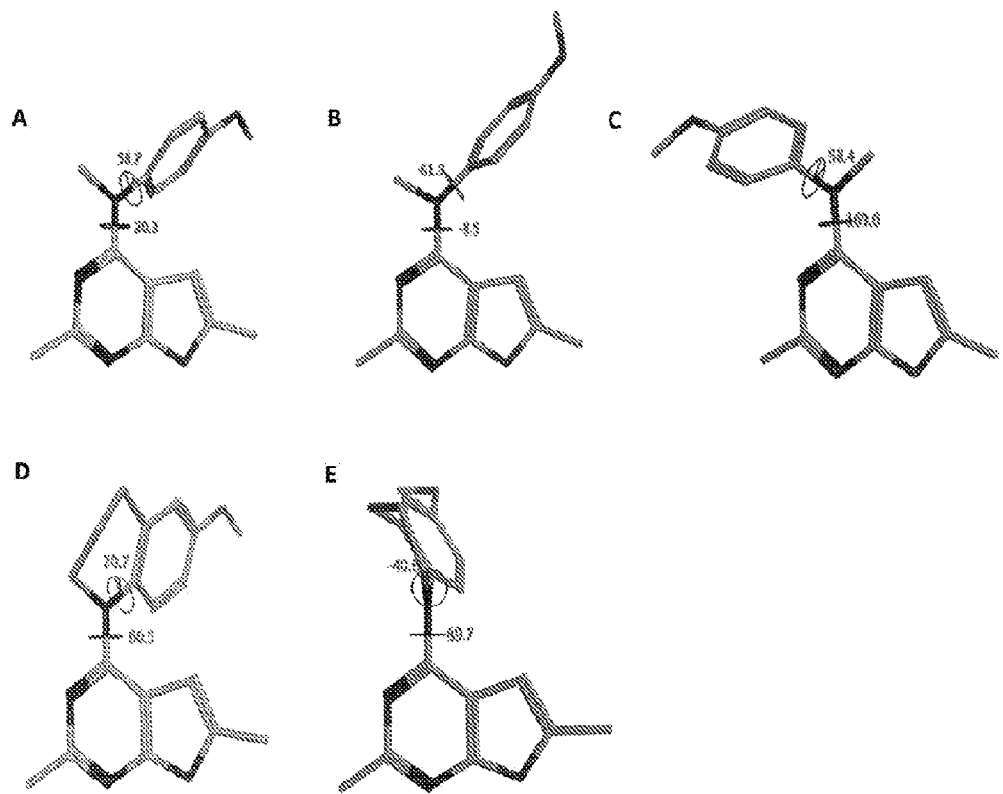
FIG. 10 shows a comparison of compound 1and compound 10 in the ATP site of VEGFR2. Lowest energy conformations of compound 1 (A) and compound 10(D) predicted by the systematic conformational search. Docked conformations of compound 1[22] in the vertical (B) and horizontal (C) binding modes and compound 10(E) in the vertical binding mode in the ATP site of VEGFR2.
Figure 11:
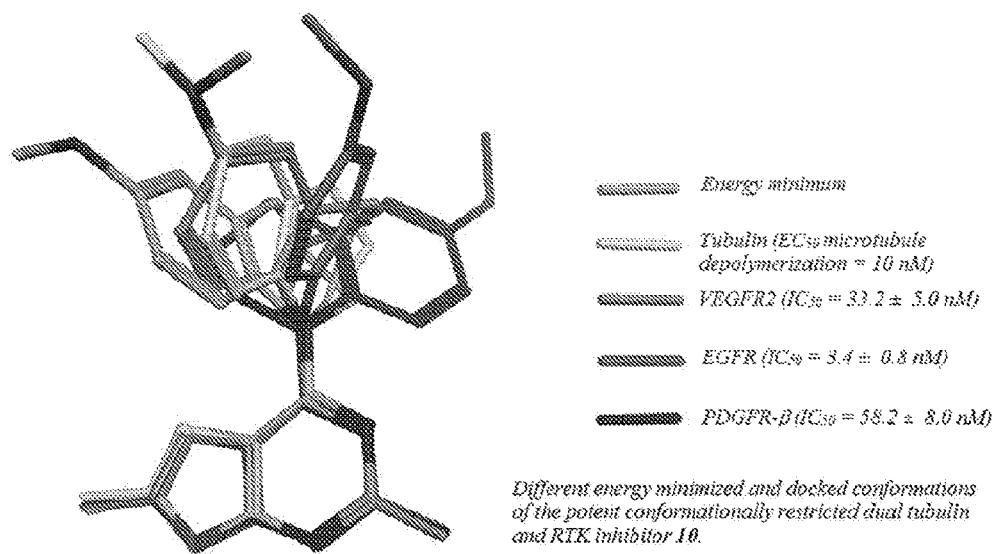
FIG. 11 shows TOC graphic and alternate TOC graphic of compound 10.
Figure 11:
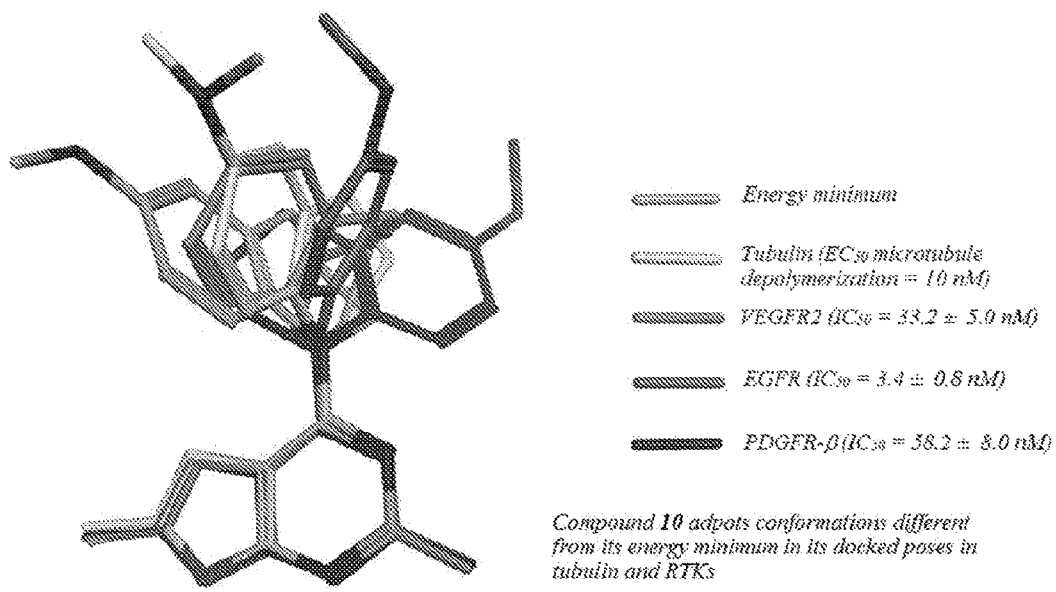

FIG. 10 shows a comparison of compound 1 and compound 10 in the ATP site of VEGFR2. FIG. 10 shows the lowest energy conformations of compound 1 (A) and compound 10 (D) predicted by the systematic conformational search. Docked conformations of compound 1[22] in the vertical (B) and horizontal (C) binding modes and compound 10 (E) in the vertical binding mode in the ATP site of VEGFR2. The poses were generated by superimposition of the furo[2,3-d]pyrimidine scaffolds of the docked and energy minimum poses and highlight differences in the orientations of the 4-position substituents.

We previously reported two possible binding modes for compound 1 that varied in the orientation of the furo[2,3-d]pyrimidine scaffold relative to the Hinge (either parallel to the Hinge, termed 'vertical' binding mode, analogous to that seen in the docked conformation of compound 10 in FIG. 6, or perpendicular to the Hinge, termed 'horizontal' binding mode) in the ATP site of VEGFR2.[22] On comparing the conformations and energies of the docked poses of compound 1 and compound 10 to the conformations obtained by the systematic search using Sybyl-X 2.1, it was observed that the docked conformations of compound 1 in its horizontal binding mode and compound 10 in its vertical binding mode were conformationally and energetically closest to the lowest energy conformations of compound 1 and compound 10 (for compound 1, ΔE between conformations A and B in FIG. 10=0.81 kcal/mol and for compound 10, ΔE between conformations D and E in FIG. 10=1.03 kcal/mol), respectively. In contrast, the predicted vertical binding mode for compound 1 was conformationally and energetically distant from the lowest energy conformation of compound 1 from the systematic search study (ΔE between conformations A and C in FIG. 10=1.78 kcal/mol). Similar results were obtained for the docked poses of compound 10 and compound 1 in EGFR and PDGFR-β and their respective low energy conformations (data not shown). These studies indicate that some flexibility in the molecule is necessary and is an important determining factor for the bioactive conformations of these compounds in RTKs and tubulin to allow adaptation of different conformations in order to function as multi-targeted inhibitors at different sites.

Chemistry

Scheme 1.
The synthesis of 4-chloro-2,6-dimethylfuro[2,3-d]pyrimidine, compound 17

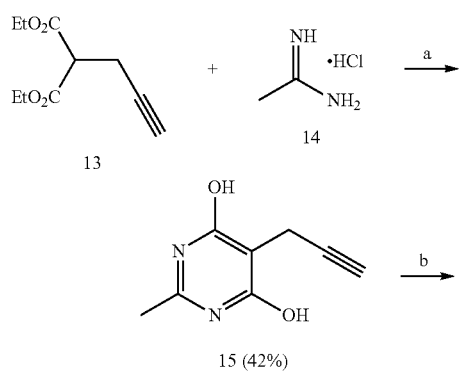

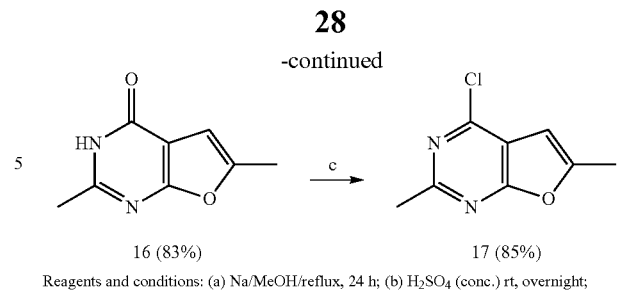

Reagents and conditions: (a) Na/MeOH/reflux, 24 h; (b) H₂SO₄ (conc.) rt, overnight; (c) POCl₃, reflux, 2 h The synthesis of the key intermediate, compound 17, is shown in Scheme 1. As we recently reported,[22] a three step reaction, starting from diethyl propargyl malonate compound 13, was successfully employed in the synthesis of 4-chloro-2,6-dimethylfuro[2,3-d]pyrimidine, compound 17 (Scheme 1). The condensation of diethyl propargyl malonate compound 13 and acetamidine hydrochloride compound 14 was carried out as a route to pyrimidine compound 15. Intramolecular cyclization of compound 15 to the furo[2,3-d]pyrimidine compound 16 (87%) proceeded under H₂SO₄ (conc.) at rt.

Scheme 2. The synthesis of N-aryl-2,6-dimethylfuro[2,3-d]pyrimidin-4-amines 2-7, 11 and 12 (i.e. compounds 2-7, 11, and 12).

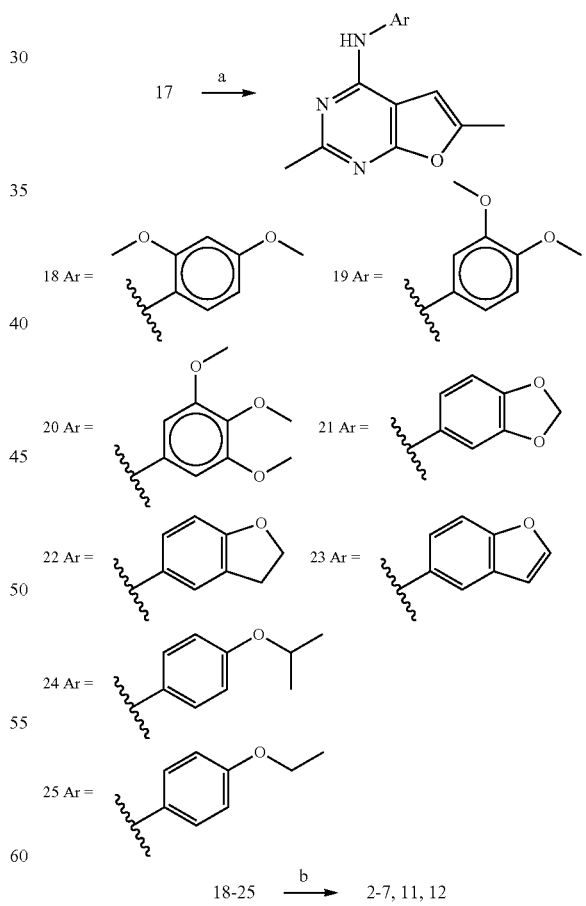

Reagents and conditions: (a) the appropriate aniline, ⁱPrOH or ⁿBuOH, 1 drop of HCl (conc.), reflux; (b) NaH, then dimethyl sulfate Chlorination of compound 16 with POCl₃ afforded the 4-chloro-2,6-dimethylfuro[2,3-d]pyrimidine compound 17.

This key intermediate was reacted with the appropriate anilines (Scheme 2), in nBuOH at reflux in the presence of a catalytic amount of HCl, to give intermediate compounds 18-125. Compounds 2-7, 11, and 12 were synthesized via N-methylation of compounds 18-25 with dimethyl sulfate in the presence of NaH (Scheme 2).

Scheme 3. The synthesis of compounds 8 and 10.

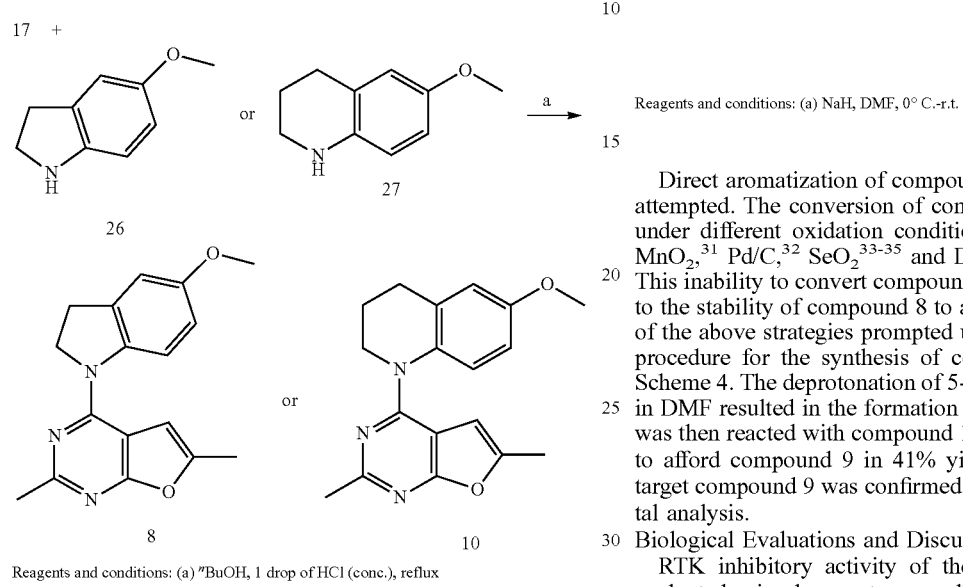

Reagents and conditions: (a) "BuOH, 1 drop of HCl (conc.), reflux

Under nucleophilic displacement condition, intermediate compound 17 (Scheme 3) reacted with compounds 26 or 27 at reflux in nBuOH and a catalytic amount of HCl to provide compound 8 or 10, respectively.

Scheme 4. The synthesis of compound 9.

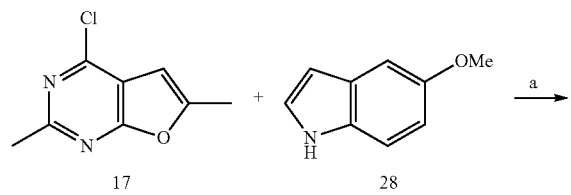

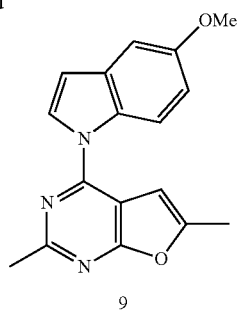

Reagents and conditions: (a) NaH, DMF, 0° C.-r.t.

Direct aromatization of compound 8 to compound 9 was attempted. The conversion of compound 8 to compound 9 under different oxidation conditions including the use of $MnO_2$,[31] $Pd/C$,[32] $SeO_2$[33-35] and $DDQ$[33-35] were unfruitful. This inability to convert compound 8 to compound 9 attests to the stability of compound 8 to aromatization. The failure of the above strategies prompted us to develop an alternate procedure for the synthesis of compound 9 as shown in Scheme 4. The deprotonation of 5-methoxyindoline by NaH in DMF resulted in the formation of a pyrrole anion, which was then reacted with compound 17 via $S_NAr$ displacement to afford compound 9 in 41% yield. The structure of the target compound 9 was confirmed by $^1H$ NMR and elemental analysis.

Biological Evaluations and Discussion

RTK inhibitory activity of the compounds 2-12 were evaluated using human tumor cells known to express high levels of EGFR, VEGFR-2 or PDFGR-β using a phosphotyrosine ELISA cytoblot, the data obtained are summarized in Table 1. Compound 1 and compounds known to inhibit a particular RTK were used as positive controls for these assays. The effects of the compounds on cell proliferation were measured in A431 cancer cells known to overexpress EGFR (Table 1). Finally, the effects of compounds 2-12 of this invention on blood vessel formation was assessed using the chicken embryo chorioallantoic membrane (CAM) assay, a standard test for angiogenesis, and the results are presented in Table 1. In the CAM assay, purified angiogenic growth factors were placed locally on a vascularized membrane of a developing chicken embryo together with compounds of interest. Digitized images of the vasculature were taken 48 h after growth factor administration and the number of vessels per unit area evaluated as a measure of vascular density.

TABLE 1

RTK, A431 and CAM inhibitory activities of compounds 1-12.

| Compound | EGFR kinase inhibition (nM) | VEGFR-2 kinase inhibition (nM) | PDGFR-β kinase inhibition (nM) | A431 Cytotoxicity (nM) | CAM angiogenesis inhibition (μM) |
|---|---|---|---|---|---|
| 1 | 68.2 ± 6.2 | 19.1 ± 3.0 | 22.8 ± 4.9 | 20.8 ± 4.2 | 3.9 ± 0.4 |
| 2 | 162.3 ± 22.2 | 32.3 ± 5.0 | 40.4 ± 5.3 | 17.1 ± 2.0 | 53.6 ± 8.4 |
| 3 | 90.3 ± 10.2 | 18.6 ± 3.0 | 66.1 ± 8.1 | 9.7 ± 1.2 | 34.8 ± 5.1 |
| 4 | >500 | >300 | 166.3 ± 20.2 | >300 | >300 |
| 5 | 298.2 ± 38.1 | 19.9 ± 2.1 | 50.1 ± 7.8 | 48.9 ± 5.1 | 38.2 ± 5.1 |
| 6 | 226.4 ± 50.2 | 6.7 ± 0.81 | 24.6 ± 4.3 | 38.3 ± 4.2 | 14.0 ± 1.7 |
| 7 | 306.6 ± 42.1 | 5.8 ± 0.73 | 25.0 ± 4.8 | 73.2 ± 10.1 | 15.2 ± 0.81 |
| 8 | 103.2 ± 18.2 | 20.9 ± 3.7 | 73.2 ± 4.9 | 42.2 ± 5.0 | 38.2 ± 4.2 |
| 9 | >500 | >300 | 198.0 ± 22.5 | >300 | >300 |
| 10 | 3.4 ± 0.8 | 33.2 ± 5.0 | 58.2 ± 8.0 | 18.0 ± 2.9 | 104.2 ± 13.2 |
| 11 | 102.2 ± 20.1 | 38.5 ± 4.7 | 84.0 ± 10.0 | 11.6 ± 2.1 | 50.1 ± 8.2 |

TABLE 1-continued

RTK, A431 and CAM inhibitory activities of compounds 1-12.

| Compound | EGFR kinase inhibition (nM) | VEGFR-2 kinase inhibition (nM) | PDGFR-β kinase inhibition (nM) | A431 Cytotoxicity (nM) | CAM angiogenesis inhibition (μM) |
|---|---|---|---|---|---|
| 12 | >500 | 121.3 ± 18.6 | 132.0 ± 14.4 | 92.9 ± 10.1 | 201.0 ± 34.9 |
| semaxanib | n.d. | 12.9 | n.d. | n.d. | 60.0 ± 10.1 |
| cisplatin | n.d. | n.d. | n.d. | 10.6 | |
| sunitinib | 172.1 ± 19.4 | 18.9 ± 2.7 | 83.1 ± 10.1 | n.d. | 1.3 ± 0.07 |
| erlotinib | 1.2 ± 0.2 | 124.7 ± 18.2 | n.d. | n.d. | 29.1 ± 1.9 | n.d. not determined

In the cellular assays using cells with high expression of EGFR, compound 10 showed similar potency as the standard erlotinib and is about 30-fold more potent than compound 1. All the other compounds (2-9, 11 and 12) were less potent than erlotinib and compound 1 in EGFR expressing cells. This result suggests that the tetrahydroquinoline ring system in compound 10 is highly favorable for EGFR inhibition and also indicates that conformational restriction by other structural constraints described above, besides the tetrahydroquinoline, were detrimental to inhibition of EGFR overexpressing tumor cells compared to compound 1.

Against VEGFR-2 expressing cells, both compounds 6 and 7 with the conformationally restricted 4'-OMe of compound 1 afforded excellent inhibitory activity, somewhat better than compound 1 and the standard semaxanib and 3-fold better than sunitinib. Conformationally restricted analogs compounds 3 and 5, with restrictions at the 4'-OMe of compound 1 are equipotent with compound 1 and sunitinib, as is compound 8 with a 5'-OMe dihydroindole substituent at the 4-position. Compounds 2, 10, and 11 are similarly potent and somewhat less potent than compound 1 and sunitinib, however they maintain two-digit nanomolar potency. Compounds 4 and 9 were relatively inactive, with compound 12 six-fold less active than compound 1. With the exception of compounds 4, 9 and 12, conformational restriction affords good potency against VEGFR-2 overexpressing cells, with some analogs better than compound 1 and the clinically used standard sunitinib.

In the PDGFR-β expressing cells, as in VEGFR-2 expressing cells, compounds 6 and 7 were the most potent and were similar to compound 1 but about 4-fold better than the standard sunitinib. Compounds 2, 5 and 10 were less potent than compound 1 but somewhat better than sunitinib. Compounds 3, 8, and 11 were similar to sunitinib but less potent than compound 1. Finally, compounds 4, 9 and 12 were the least potent, but possessed three-digit nanomolar $IC_{50}$ values. Thus, like VEGFR-2, with the exception of compounds 4, 9 and 12, conformational restriction of compound 1 was conducive to PDGFR-□ inhibition.

Against A431 cells all of the analogs (with compound 4 as an exception) maintain good activity compared to compound 1 and within 2- to 3-fold less potent than compound 1. In the CAM angiogenesis assay all of the compounds showed activity, with compounds 6 and 7 being most potent and compounds 4, 10, and 12 the least potent.

TABLE 2

Microtubule depolymerizing and antiproliferative activities ($IC_{50}$ ± SD) of compounds 2-12.

| Compound | $EC_{50}$ for MT depolymerization in A · 10 cells (nM) | $IC_{50}$ ± SD in MDA-435 cells (nM) | $EC_{50}/IC_{50}$ ratio | $IC_{50}$ ± SD in HeLa (nM) | $IC_{50}$ ± SD in WTβ3 (nM) | Rr value | $IC_{50}$ ± SD in SKOV3 cells (nM) | $IC_{50}$ ± SD in M6/6 cells (nM) | Rr value |
|---|---|---|---|---|---|---|---|---|---|
| 1* | 103 | 17.1 ± 1.5 | 6 | 33.1 ± 1.6 | 27.2 | 0.8 | 36.7 ± 2.3 | 63.3 ± 4.8 | 1.7 |
| 2 | 2,994 | 139.5 ± 8.8 | 22 | 321.4 ± 71.3 | 235.7 ± 10.6 | 0.7 | 372.3 ± 26.2 | 482.9 ± 18.5 | 1.3 |
| 3 | 2,719 | 50.6 ± 7.6 | 54 | 122.7 ± 10.1 | 113.1 ± 26.4 | 0.9 | 129.0 ± 14.2 | 203.3 ± 0.6 | 1.6 |
| 4 | >10,000 | n.d. | n.d. | n.d. | n.d. | n.d. | n.d. | n.d. | n.d. |
| 5 | >10,000 | n.d. | n.d. | n.d. | n.d. | n.d. | n.d. | n.d. | n.d. |
| 6 | 606 | 96.2 ± 13 | 6 | 104.6 ± 5.8 | 94.0 ± 7.0 | 0.9 | 120.5 ± 5.0 | 155.2 ± 17.2 | 1.3 |
| 7 | 3,786 | 133 ± 1.7 | 28 | 301.8 ± 23.4 | 242.7 ± 15.1 | 0.8 | 425.3 ± 53.1 | 509.0 ± 4.8 | 1.2 |
| 8 | >10,000 | n.d. | n.d. | n.d. | n.d. | n.d. | n.d. | n.d. | n.d. |
| 9 | >10,000 | n.d. | n.d. | n.d. | n.d. | n.d. | n.d. | n.d. | n.d. |
| 10 | 21 | 9.8 ± 0.9 | 2 | 13.5 ± 0.5 | 9.1 ± 1.8 | 0.7 | 12.9 ± 1.2 | 19.4 ± 2.9 | 1.5 |
| 11 | >10,000 | n.d. | n.d. | n.d. | n.d. | n.d. | n.d. | n.d. | n.d. |
| 12 | 182 | 13.4 ± 1.6 | 14 | 28.2 ± 0.7 | 19.4 ± 0.7 | 0.7 | 24.6 ± 5.1 | 30.8 ± 1.7 | 1.3 |
| CA-4 | 9.8 | 5.0 ± 0.3 | 2 | 5.6 ± 0.3 | 5.7 ± 0.4 | 1.0 | 6.9 ± 0.1 | 3.0 ± 0.3 | 0.4 |
| Paclitaxel | n.d. | 3.3 ± 0.3 | n.d. | 1.9 ± 0.3 | 32.9 ± 5.8 | 17.3 | 6.3 ± 0.4 | 1,187.2 ± 265.2 | 265.2 | n.d. not determined

The ability of compounds 2-12 to cause dose-dependent loss of cellular microtubules were evaluated and the data summarized in Table 2 in comparison with the data obtained with compound 1 and CA-4 as control. Compounds 2, 3, 6, 7, 10 and 12 showed dose-dependent loss of cellular microtubules. Among these compounds, compound 10 had an $EC_{50}$ of 21 nM, which is 5- to 10-fold more potent than all the other analogs including compound 1and comparable to CA-4. The second most potent new compound was compound 12 and the third most active was compound 6. Compounds 2, 3 and 7 were significantly less potent. With compound 10, it appears that an optimal restriction in conformation can lead to an increased effect on cellular microtubules, while in compounds 4, 5, 8, 9 and 11 perhaps the bulk and/or conformational rigidity prevents anti-microtubule activity. Although compound 8 showed good RTK inhibition, it has no effect on cellular microtubules. Structure-activity analyses of all the members of this series identified that the conformation of the compounds do affect potency as disruptors of cellular microtubules (Table 2), and this activity is independent of the bioactive conformation required for RTK inhibition.

Comparing the biological activities of compounds 2-4 against RTKs and tubulin (Tables 1 and 2) suggests that increasing the energy barrier for rotation by introducing bulky groups adjacent to the rotatable σ bonds is, with the exception of A431 cells where compounds 2 and 3 show improved activities, detrimental to biological activity in RTKs and tubulin compared to compound 1. However, the extent of the loss of activity of compounds 2-14 in RTKs is less than that against tubulin. This indicates that the ability to rotate bonds a-c to achieve the bioactive conformations of these compounds is of greater importance against tubulin than RTKs.

Compounds 5-7, where the design strategy was to restrict rotation of bond c by incorporation into a ring, show improved activities against VEGFR2 (compounds 6 and 7), but lose activity against EGFR, PDGFR-□ and tubulin. Comparing compounds 8-10, in which both bonds a and b are restricted by incorporation in a ring, shows that complete restriction of rotation in compound 9 eliminates RTK as well as tubulin inhibitory activities. Increasing flexibility around bond a in compound 8 restores some of the lost inhibitory activity against both RTK and tubulin. The most flexible of compounds 8-10, compound 10, shows improved activities in EGFR and tubulin compared to compound 1 once again indicating that some flexibility is necessary for dual RTK/tubulin inhibitory effects.

Compounds 11 and 12 that were designed to explore the effect of bulk at the 4'-position of the aniline moiety show loss of activities against RTKs compared to compound 1. However, compound 12 shows improved potency in most of the tubulin assays (Table 2) compared to compound 1, indicating that bulk at the 4'-position is beneficial for anti-tubulin activity.

The ability to circumvent drug resistance mechanisms is a notable advantage of colchicine site agents, and the effects of compounds 2-12 were evaluated in two pairs of multidrug resistant cells (Table 2). The microtubule active compounds were evaluated in the parental HeLa cells and in an engineered cell line overexpressing □III tubulin (WT□3). The cells were equally sensitive to each of the compounds, with relative resistance values of 0.7-0.9. In addition, the compounds were evaluated for their ability to inhibit the growth of SK-OV-3 cells expressing Pgp were evaluated and compared to the parental line (Table 2). The relative resistance values range from 1.2-1.6, while the relative resistance of the Pgp substrate paclitaxel was over 250. These results demonstrate that compounds 2, 3, 6, 7, 10 and 12 overcome both □III and Pgp mediated drug resistance mechanisms.

TABLE 3

Effects of compound 10 on tubulin polymerization and inhibition of colchicine binding.

| Compound | Inhibition tubulin assembly $IC_{50}$ (μM) ± SD | Inhibition of colchicine binding % inhibition ± SD | |
|---|---|---|---|
| | | 1 μM | 5 μM |
| CA-4 | 1.0 ± 0.09 | 88 ± 2 | 99 ± 0.2 |
| 1 | 2.4 ± 0.01 | 63 ± 5 | 88 ± 3 |
| 10 | 1.1 ± 0.1 | 82 ± 3 | 96 ± 1 |

To our knowledge, of all the compounds having dual RTK inhibition and microtubule disrupting activity, compound 10 showed the best EGFR inhibition and anti-microtubule activity. Studies were conducted to determine if compound 10 interacted directly with purified tubulin. The $IC_{50}$ of compound 10 was determined for inhibition of tubulin polymerization as compared to the $IC_{50}$ of CA-4 and compound 1. In this assay, compound 10 inhibited tubulin assembly about as well as CA-4 (Table 3) and better than compound 1. The data in Table 4 also showed that compound 10 binds at the colchicine site on tubulin, since it inhibited [$^3$H]colchicine binding to the protein as potently as CA-4.

TABLE 4

Cancer cell inhibitory activity ($GI_{50}$, nM) of compounds 1, 6, 7 and 10 (NCI 60 cell line panel).

| Panel/Cell line | $GI_{50}$ (nM) | | | |
|---|---|---|---|---|
| | 1 | 6 | 7 | 10 |
| NSCLC | | | | |
| A549/ATCC | 37.6 | n.d. | n.d. | <10 |
| EKVX | 64.8 | 70 | 396 | <10 |
| HOP-62 | 32.2 | 39.6 | 75.2 | <10 |
| HOP-92 | n.d. | 45.8 | 226 | 58.6 |
| NCI-H226 | 84.1 | 162 | 217 | 13 |
| NCI-H23 | 40.7 | 43.9 | 206 | <10 |
| NCI-H322M | n.d. | n.d. | n.d. | <10 |
| NCI-H460 | 33.1 | 42.0 | 138 | <10 |
| NCI-H522 | <10 | 12.9 | 29.9 | <10 |
| CNS Cancer | | | | |
| SF-268 | 33.6 | 13.9 | 527 | 16.8 |
| SF-295 | 13.8 | 30.5 | 41.7 | <10 |
| SF-539 | 20.0 | 31.6 | 60.9 | <10 |
| SNB-19 | 33.3 | 56.5 | 93.6 | <10 |
| SNB-75 | 53.2 | 30.4 | 103 | <10 |
| U251 | 30.8 | 39.7 | 84 | <10 |
| Ovarian cancer | | | | |
| IGROV1 | n.d. | 62.9 | 142 | <10 |
| OVCAR-3 | 29.1 | 24.5 | 30 | <10 |
| OVCAR-4 | 60.4 | 83.4 | 553 | 51 |
| OVCAR-5 | 55.8 | 262 | 531 | 43 |
| OVCAR-8 | 36.6 | 63 | 330 | <10 |
| NCI/ADR-RES | n.d. | 26.5 | 37.6 | <10 |
| SK-OV-3 | 25.2 | 37.6 | 98.0 | <10 |
| Melanoma | | | | |
| LOX IMVI | 54.9 | 45.6 | 162 | <10 |
| MALME- | 42.3 | n.d. | n.d. | <10 |

TABLE 4-continued

Cancer cell inhibitory activity ($GI_{50}$, nM) of compounds 1, 6, 7 and 10 (NCI 60 cell line panel).

| Panel/Cell line | $GI_{50}$ (nM) | | | |
|---|---|---|---|---|
| | 1 | 6 | 7 | 10 |
| 3M | | | | |
| M14 | 23.3 | 34.8 | 47.3 | <10 |
| MDA-MB-435 | n.d. | 14.0 | 21.1 | <10 |
| SK-MEL-2 | 33.9 | 26.4 | 82.4 | <10 |
| SK-MEL-28 | 37.7 | n.d. | n.d. | <10 |
| SK-MEL-5 | 22.9 | 31.4 | 50.4 | <10 |
| UACC-62 | 14.6 | 61.3 | 57.1 | <10 |
| Renal Cancer | | | | |
| 786-0 | 43.6 | 80.4 | 1040 | <10 |
| A498 | 19.5 | n.d. | n.d. | <10 |
| ACHN | 55.9 | 64.2 | 265 | <10 |
| CAKI-1 | 16.3 | 40.1 | 57.9 | <10 |
| RXF 393 | n.d. | 21.2 | 57.2 | <10 |
| SN 12C | 56.7 | 97.2 | 611 | <10 |
| TK-10 | n.d. | 50.2 | 382 | <10 |
| UO-31 | 75.2 | n.d. | 278 | <10 |
| Colon Cancer | | | | |
| COLO 205 | 20 | 40.3 | 139 | <10 |
| HCC-2998 | 28.5 | 54.4 | 185 | 12.0 |
| HCT-116 | 34 | 45.1 | 77.1 | <10 |
| HCT-15 | 25.3 | 38.9 | 51.9 | <10 |
| HT29 | 32.5 | 32.4 | 51.9 | <10 |
| KM12 | 21.1 | 40.1 | 58.4 | <10 |
| SW-620 | 29.8 | 41.6 | 58.8 | <10 |
| Prostate Cancer | | | | |
| PC-3 | n.d. | 52.2 | 183 | <10 |
| DU-145 | 26.2 | 44.1 | 198 | <10 |
| Breast Cancer | | | | |
| MCF7 | 42.2 | 40.2 | 43.8 | <10 |
| MDA-MB-231/ATCC | 44.3 | 148 | 223 | 11.4 |
| HS 578T | 15.3 | 31.0 | 51.7 | <10 |
| BT-549 | 48.0 | 77.2 | 432 | <10 |
| MDA-MB-468 | 34.9 | 22.1 | 31.5 | <10 |
| Leukemia | | | | |
| CCRF-CEM | 25.3 | 58.1 | 121 | <10 |
| HL-60(TB) | 17.3 | 27.6 | 41.2 | <10 |
| K-562 | 13.2 | 31.7 | 40.4 | <10 |
| MOLT-4 | 67.9 | 76.7 | 211 | 15.0 |
| RPMI-8226 | 42.8 | 54.2 | 389 | <10 |
| SR | 32.0 | 36.6 | 62.4 | n.d. | n.d. not determined

Compounds 6 and 10, the most potent microtubule depolymerization agents in the current study, and compound 7 for comparison, were selected by the National Cancer Institute for evaluation in the NCI 60 cell line panel and compared with compound 1. All the three compounds (6, 7 and 10) showed potent $GI_{50}$s against most of the NCI 60 cancer cell lines (Table 4). Although compounds 6 and 7 were less potent than compound 1 in most cancer cell lines, compound 10 showed a significantly improved potency against all of the tumor cells compared to compound 1.

A series of eleven furo[2,3-d]pyrimidine compounds was designed and evaluated as dual multi-targeted RTK inhibitors and antimitotic agents, using a conformational restriction strategy. Compounds 8 and 10 showed EGFR inhibitory activity similar or better than the parent analog compound 1 while inhibition of VEGFR2 and PDGFR-β were less potent than compound 1. Remarkably, six of the compounds (2, 3, 6-8, 10 and 12) provide tubulin inhibitory activities and cytotoxic activities. As typified by compound 8, the bioactive conformation for RTK inhibition is predicted to be independent of the bioactive conformation required for tubulin inhibition. The preferred conformation of the tetrahydroquinoline substituted analog compound 10 is optimal for EGFR as well as tubulin inhibition. Compound 10 is more potent than the lead compound 1 for both EGFR (20-fold) and tubulin (5-fold) inhibition, but not for all RTKs or antiangiogenic activities, indicating that the bioactive conformation in furo[2,3-d]pyrimidine analogs for dual RTK and tubulin inhibitory activities vary. This indicates that suitable conformational restriction increases potency for both tubulin and EGFR without loss of activity against VEGFR2 and PDGFR-β. Among multi-targeted inhibitors the best analog is selected on the basis of the compound that has the best balance in inhibitory activities against the various targets. For this series compound 10 was the best analog as evidenced by the activities in the NCI-60 tumor cell panel (Table 4) where it supersedes the activity of the parent compound 1.

EXPERIMENTAL SECTION

All evaporations were carried out in vacuo with a rotary evaporator. Analytical samples were dried in vacuo (0.2 mmHg) in a CHEM-DRY drying apparatus over $P_2O_5$ at 55° C. Melting points were determined on a MEL-TEMP II melting point apparatus with FLUKE 51 K/J electronic thermometer and are uncorrected. Proton nuclear magnetic resonance ($^1$H NMR) spectra were recorded on a Bruker WH-300 (300 MHz) or a Bruker 400 MHz/52 MM (400 MHz) spectrometer. The chemical shift values are expressed in ppm (parts per million) relative to tetramethylsilane as internal standard: s) singlet, d) doublet, t) triplet, q) quartet, m) mutiplet, br) broad singlet. The relative integrals of peak areas agreed with those expected for the assigned structures. High resolution mass spectra (HRMS), using Electron Impact (EI), were recorded on a VG AUTOSPEC (Fisons Instruments) micromass (EBE Geometry) double focusing mass spectrometer. Thin-layer chromatography (TLC) was performed on Whatman Sil G/UV254 silica gel plates with fluorescent indicator, and the spots were visualized under 254 and 366 nm illumination. Proportions of solvents used for TLC are by volume. Column chromatography was performed on a 230-400 mesh silica gel (Fisher, Somerville, N.J.) column. Elemental analyses were performed by Atlantic Microlab, Inc., Norcross, Ga. Element compositions were within ±0.4% of the calculated values. Fractional moles of water or organic solvents found in some analytical samples could not be prevented despite 24-48 h of drying in vacuo and were confirmed where possible by their presence in the $^1$H NMR spectra. All solvents and chemicals were purchased from Aldrich Chemical Co. or Fisher Scientific and were used as received. Purities of the final compounds 2-10 were >95% by elemental analysis. Hereinafter, each compound will be referred to their hereinbefore identified number, respectively (i.e., for example, 15 refers to compound 15).

2-Methyl-6-hydroxy-5-prop-2-yn-1-ylpyrimidin-4 (3H)-one (15)

A mixture of diethyl prop-2-yn-1-ylmalonate 13 (11.9 g, 60 mmol), sodium metal (1.38 g, 60 mmol) and acetamidine hydrochloride 14 (5.68 g, 60 mmol) was heated to reflux in MeOH (100 mL) for 24 h. The suspension was then cooled in an ice-bath to room temperature. The precipitate formed was collected by filtration and dissolved in 40 mL of water. This solution was adjusted to pH 3-4 with 1 N HCl, whereupon a thick precipitate formed. The mixture was filtered, and the filtrate was washed with a small amount of water and acetone and dried over $P_2O_5$ to afford 4.1 g (42%) of 15 as a white solid; mp>300° C.; $R_f$ 0.11 ($CHCl_3$/MeOH 6:1); $^1$H NMR (DMSO-$d_6$) δ 2.23 (s, 3H), 3.05 (s, 2H), 3.32 (s, 1H), 11.92 (s, 2H).

2,6-Dimethylfuro[2,3-d]pyrimidin-4(3H)-one (16)

To a 25 mL round-bottomed flask were added 15 (1.64 g, 10 mmol) and concentrated sulfuric acid (15 mL). The resulting solution was stirred overnight and poured into 100 mL distilled water and extracted times by chloroform (3×30 mL). The organic layers were pooled and concentrated to afford 16 (1.36 g, 83%) as a yellow powder; mp>300° C.; $R_f$ 0.35 ($CHCl_3$/MeOH 6:1); $^1$H NMR (DMSO-$d_6$) δ 2.42 (s, 3H, $CH_3$), 2.44 (s, 3H, $CH_3$), 6.63 (s, 1H, CH), 12.50 (s, 1H, 3-NH exch).

4-Chloro-2,6-dimethylfuro[2,3-d]pyrimidine (17)

To a 50 mL flask were added 16 (1.64 g, 1 mmol) and 10 mL $POCl_3$. The resulting mixture was refluxed for 2 h, and the solvent was removed under reduced pressure to afford a dark residue. The crude mixture was purified by silica gel column chromatography using AcOEt/Hexane=20:1 as the eluent. Fractions containing the product (TLC) were combined and evaporated to afford 1.55 g (85%) 17 as a yellow solid; mp 47.6-48.1° C.; $R_f$ 0.26 (AcOEt/Hexane 15:1); $^1$H NMR (DMSO-$d_6$) δ 2.48 (s, 3H), 2.63 (s, 3H), 6.77 (s, 1H).

General Procedure for the Synthesis of 18-25 (Compounds 18-25)

To a 100-mL round-bottomed flask, flushed with nitrogen, were added 17 (127 mg, 0.7 mmol), the appropriate aniline (1.05 mmol), BuOH (20 mL), and 2-3 drops of conc. HCl. The reaction mixture was heated at reflux with stirring for 2 h until the starting material 17 disappeared (TLC). The reaction solution was allowed to cool to room temperature; the solvent was removed under reduced pressure, and the residue was purified by column chromatography on silica gel with 10% AcOEt/Hexane as the eluent. Fractions containing the product (TLC) were combined and evaporated to afford target compounds.

N-(2,4-dimethoxyphenyl)-2,6-dimethylfuro[2,3-d]pyrimidin-4-amine (18)

Using the general procedure described above, compound 18 (77%) was obtained as an off-white powder; mp 97.7-97.9° C.; $R_f$ 0.62 (AcOEt/Hexane 1:1); $^1$H NMR (DMSO-$d_6$) δ 2.31 (s, 3H), 2.37 (s, 3H), 3.73 (s, 3H, $OCH_3$), 3.81 (s, 3H, $OCH_3$), 5.93 (s, 1H, 5-CH), 6.55-6.58 (dd, 1H, J=6.8 Hz, J=2 Hz $C_6H_3$), 7.33-7.35 (d, 2H, J=6.8 Hz, $C_6H_3$), 8.78 (s, 1H, NH exch), Anal. $C_{16}H_{17}N_3O_3$.

N-(3,4-dimethoxyphenyl)-2,6-dimethylfuro[2,3-d]pyrimidin-4-amine (19)

Using the general procedure described above, compound 19 (82%) was obtained as a gray solid; mp 150.8-151.4° C.; $R_f$ 0.50 (AcOEt/Hexane 1:1); $^1$H NMR (DMSO-$d_6$) δ 2.41 (s, 3H), 2.48 (s, 3H), 3.75 (s, 3H, $OCH_3$), 3.78 (s, 3H, $OCH_3$), 6.57 (s, 1H, 5-CH), 6.94-6.96 (d, 1H, J=7.2 Hz, $C_6H_3$), 7.24-7.26 (dd, 1H, J=7.2 Hz, $C_6H_3$), 7.54 (s, 1H), 9.36 (s, 1H, NH exch), Anal. $C_{16}H_{17}N_3O_3 \cdot H_2O$.

2,6-Dimethyl-N-(3,4,5-trimethoxyphenyl)furo[2,3-d]pyrimidin-4-amine (20)

Using the general procedure described above, compound 20 (83%) was obtained as a yellow powder; mp 173.5-173.7° C.; $R_f$ 0.03 (AcOEt/Hexane 3:1); $^1$H NMR (DMSO-$d_6$) δ 2.43 (s, 3H), 2.50 (s, 3H), 3.65 (s, 3H, $OCH_3$), 3.80 (s, 6H, 2 $OCH_3$), 6.71 (s, 1H, 5-CH), 7.29 (s, 2H, $C_6H_2$), 9.43 (s, 1H, NH exch), Anal. $C_{17}H_{19}N_3O_4 \cdot 0.2H_2O$.

N-1,3-benzodioxol-5-yl-2,6-dimethylfuro[2,3-d]pyrimidin-4-amine (21)

Using the general procedure described above, compound 21 (72%) was obtained as a brown solid; mp 185.5-187.1° C.; $R_f$ 0.10 (Hexane/EtOAC 3:1); $^1$H NMR (DMSO-$d_6$) δ 2.40 (s, 3H, $CH_3$), 2.46 (s, 3H, $CH_3$), 6.01 (s, 2H, $OCH_2O$), 6.59 (br, 1H, NH exch), 6.89-6.91 (d, 1H, J=6.8 Hz), 7.09-7.11 (dd, 1H, J=8.4 Hz), 7.51 (s, 1H), 9.37 (s, 1H), Anal. $C_{15}H_{13}N_3O_2$.

N-(2,3-dihydro-1-benzofuran-5-yl)-2,6-dimethylfuro[2,3-d]pyrimidin-4-amine (22)

Using the general procedure described above, compound 22 (70%) was obtained as a brown solid; mp 193.7-195.2° C.; $R_f$ 0.10 (Hexane/EtOAC 3:1); $^1$H NMR (DMSO-$d_6$) δ 2.38 (s, 3H, $CH_3$), 2.44 (s, 3H, $CH_3$), 3.18-3.23 (t, 2H, J=8.4 Hz, $CH_2CH_2$), 4.52-4.56 (t, 2H, J=8.4 Hz, $CH_2CH_2$), 6.43 (br, 1H, NH exch), 6.74-6.77 (d, 1H, J=8.4 Hz), 7.33-7.35 (d, 1H, J=8.4 Hz), 7.57 (s, 1H), 9.50 (s, 1H), Anal. $C_{16}H_{15}N_3O_2$.

N-1-benzofuran-5-yl-2,6-dimethylfuro[2,3-d]pyrimidin-4-amine (23)

Using the general procedure described above, compound 23 (66%) was obtained as a colorless crystal; mp 173.4-175.0° C.; $R_f$ 0.10 (Hexane/EtOAC 3:1); $^1$H NMR (DMSO-$d_6$) δ 2.40 (s, 3H, 6-$CH_3$), 2.49 (s, 3H, 2-$CH_3$), 6.55 (br, 1H, NH exch), 6.98 (d, 1H, J=1.6 Hz, 5-CH), 7.58-7.60 (d, 2H, $C_8H_5$), 7.99 (d, 1H, $C_8H_5$), 8.11-8.13 (t, 1H, $C_8H_5$), 9.50 (s, 1H, $C_8H_5$), Anal. $C_{16}H_{13}N_3O_2$.

N-(4-ethoxyphenyl)-2,6-dimethylfuro[2,3-d]pyrimidin-4-amine (24)

Using the general procedure described above, compound 24 (80%) was obtained as an off-white powder; mp 160.6-162.1° C.; $R_f$ 0.51 (Hexane/EtOAc 3:1); $^1$H NMR (DMSO-$d_6$) δ 1.32-1.35 (t, 3H, J=5.6 Hz, $OCH_2CH_3$), 2.40 (s, 3H, 6-$CH_3$), 2.45 (s, 3H, 2-$CH_3$), 4.00-4.04 (q, 2H, J=5.6 Hz, $OCH_2CH_3$), 6.50 (s, 1H, 5-CH), 6.93-6.94 (d, 2H, J=6.8 Hz, $C_6H_4$), 7.61 (d, 2H, J=6.8 Hz, $C_6H_4$), 9.34 (s, 1H, NH exch); Anal. $C_{16}H_{17}N_3O_2$.

2,6-Dimethyl-N-(4-propoxyphenyl)furo[2,3-d]pyrimidin-4-amine (25)

Using the general procedure described above, compound 25 (67%) was obtained as a colorless crystal; mp 136.3-

137.1° C.; $R_f$ 0.51 (Hexane/EtOAC 3:1); $^1$H NMR (DMSO-d$_6$) δ 0.98-1.00 (t, 3H, OCH$_2$CH$_2$CH$_3$), 1.70-1.77 (m, 2H, OCH$_2$CH$_2$CH$_3$), 2.40 (s, 3H, 6-CH$_3$), 2.45 (s, 3H, 2-CH$_3$), 3.91-3.94 (t, 2H, OCH$_2$CH$_2$CH$_3$), 6.53 (s, 1H, 5-CH), 6.93-6.94 (d, 2H, J=7.2 Hz, C$_6$H$_4$), 7.61-7.62 (d, 2H, J=7.2 Hz, C$_6$H$_4$), 9.33 (s, 1H, NH exch); Anal. C$_{17}$H$_{19}$N$_3$O$_2$.

General Procedure for the Synthesis of 2-7, 11 and 12

To a 25 mL round bottomed flask was weighed 18-25 (0.5 mmol) and was added DMF (2 mL) to afford a solution. The flask was purged with argon for five min, followed by cooling to 0° C. using ice bath. Sodium hydride (36 mg, 1.5 mmol) was added to the solution at 0° C. The solution was stirred for 30 min at 0° C. under argon atmosphere. Dimethyl sulfate (150 mg, 1.2 mmol) was introduced to the reaction mixture with the help of a syringe and the flask was warmed to room temperature. The mixture was stirred at room temperature for another 3 h and 5 mL of 1 N HCl was added carefully to quench the reaction. The reaction solvent was removed under reduced pressure and the residue was suspended in water (20 mL). The suspension was extracted using ethyl acetate (2×10 mL). The combined organic extracts were washed with brine (10 mL), dried over anhydrous sodium sulfate and removed by evaporation under reduced pressure. The residue was purified by column chromatography on silica gel with 20% AcOEt/Hexane as the eluent. Fractions containing the product (TLC) were combined and evaporated to afford target compounds.

N-(2,4-dimethoxyphenyl)-N,2,6-trimethylfuro[2,3-d]pyrimidin-4-amine (2)

Using the general procedure described above, compound 2 (74%) was obtained as orange crystals: mp 166.1-166.4° C.; $R_f$ 0.38 (AcOEt/Hexane, 1:1); $^1$H NMR (DMSO-d6) δ 2.16 (s, 3H, CH$_3$), 2.47 (s, 3H, CH$_3$), 3.41 (s, 3H, NCH$_3$), 3.70 (s, 3H, OCH$_3$), 3.85 (s, 3H, OCH$_3$), 4.57 (s, 1H, 5-CH), 6.62-6.64 (dd, 1H, J=6.8 Hz, J=2.0 Hz, C$_6$H$_3$), 6.75-6.76 (d, 1H, J=6.8 Hz, C$_6$H$_3$), 7.24-7.22 (d, 1H, J=2.0 Hz, C$_6$H$_3$), Anal. C$_{17}$H$_{19}$N$_3$O.

N-(3,4-dimethoxyphenyl)-N,2,6-trimethylfuro[2,3-d]pyrimidin-4-amine (3)

Using the general procedure described above, compound 3 (50%) was obtained as an orange crystal: mp 114.2-116.6° C.; $R_f$ 0.28 (AcOEt/Hexane, 1:1); $^1$H NMR (DMSO-d6) δ 2.17 (s, 3H, CH$_3$), 2.48 (s, 3H, CH$_3$), 3.47 (s, 3H, NCH$_3$), 3.73 (s, 3H, OCH$_3$), 3.82 (s, 3H, OCH$_3$), 4.64 (s, 1H, 5-CH), 6.87-6.89 (dd, 1H, J=6.8 Hz, J=2.0 Hz, C$_6$H$_3$), 7.02-7.07 (d, 1H, J=2.0 Hz, C$_6$H$_3$), 7.04-7.06 (d, 1H, J=6.8 Hz, C$_6$H$_3$), Anal. C$_{17}$H$_{19}$N$_3$O$_3$.

N,2,6-trimethyl-N-(3,4,5-trimethoxyphenyl)furo[2,3-d]pyrimidin-4-amine (4)

Using the general procedure described above, compound 4 (63%) was obtained as light yellow crystals: mp 176.5-178.1° C.; $R_f$ 0.19 (AcOEt/Hexane, 2:1); $^1$H NMR (DMSO-d6) δ 2.20 (s, 3H, CH$_3$), 2.49 (s, 3H, CH$_3$), 3.50 (s, 3H, NCH$_3$), 3.74 (s, 9H, 3 OCH$_3$), 4.73 (s, 1H, 5-CH), 6.73 (s, 2H, C$_6$H$_2$), Anal. C$_{18}$H$_{21}$N$_3$O$_4$.

N-1,3-benzodioxol-5-yl-N,2,6-trimethylfuro[2,3-d]pyrimidin-4-amine (5)

Using the general procedure described above, compound 5 (67%) was obtained as colorless crystals; mp 200.0-200.7° C.; $R_f$ 0.48 (AcOEt/Hexane 1:1); $^1$H NMR (DMSO-d$_6$) δ 2.21 (s, 3H, CH$_3$), 2.48 (s, 3H, CH$_3$), 3.44 (s, 3H, OCH$_3$), 4.76 (s, 1H, 5-CH), 6.14 (s, 2H, OCH$_2$O), 6.82-6.84 (m, 1H), 7.01-7.04 (m, 2H), Anal. C$_{16}$H$_{15}$N$_3$O$_3$.

N-(2,3-dihydro-1-benzofuran-5-yl)-N,2,6-trimethylfuro[2,3-d]pyrimidin-4-amine (6)

Using the general procedure described above, compound 6 (59%) was obtained as colorless crystals; mp 167.2-168.4° C.; $R_f$ 0.16 (AcOEt/Hexane 3:1); $^1$H NMR (DMSO-d$_6$) δ 2.18 (s, 3H, CH$_3$), 2.48 (s, 3H, CH$_3$), 3.21-3.25 (t, 2H, J=6.8 Hz, CH$_2$CH$_2$), 3.45 (s, 3H, OCH$_3$), 4.61-4.64 (t, 2H, J=6.8 Hz, CH$_2$CH$_2$), 4.65 (s, 1H, 5-CH), 6.86-6.88 (d, 1H, J=6.8 Hz), 7.05-7.07 (dd, 1H, J=8.4 Hz), 7.24 (s, 1H), Anal. C$_{17}$H$_{17}$N$_3$O$_2$.

N-1-benzofuran-5-yl-N,2,6-trimethylfuro[2,3-d]pyrimidin-4-amine (7)

Using the general procedure described above, compound 7 (63%) was obtained as a colorless crystal; mp 193.0-194.2° C.; $R_f$ 0.22 (AcOEt/Hexane 3:1); $^1$H NMR (DMSO-d$_6$) δ 2.10 (s, 3H, CH$_3$), δ 2.49 (s, 3H, CH$_3$), 3.38 (s, 3H, OCH$_3$), 4.37 (s, 1H, 5-CH), 7.03 (s, 1H), 7.30-7.32 (d, 1H, J=6.8 Hz), 7.69 (s, 1H), 7.74-7.76 (d, 1H, J=6.8 Hz), 8.13 (s, 1H), Anal. C$_{17}$H$_{15}$N$_3$O$_2$.

N-(4-ethoxyphenyl)-N,2,6-trimethylfuro[2,3-d]pyrimidin-4-amine (11)

Using the general procedure described above, compound 11 (49%) was obtained as a colorless crystal: mp 107.6-108.2° C.; $R_f$ 0.64 (AcOEt/Hexane, 1:3); $^1$H NMR (DMSO-d6) δ 1.36-1.38 (t, 3H, J=5.6 Hz, OCH$_2$CH$_3$), 2.16 (s, 3H, CH$_3$), 2.48 (s, 3H, CH$_3$), 3.45 (s, 3H, NCH$_3$), 4.85-4.10 (q, 2H, OCH$_2$CH$_3$), 4.58 (s, 1H, 5-CH), 7.04-7.06 (d, 2H, J=7.2 Hz, C$_6$H$_4$), 7.26-7.28 (d, 2H, J=7.2 Hz, C$_6$H$_4$); Anal. C$_{17}$H$_{19}$N$_3$O$_2$.

N-2,6-trimethyl-N-(4-propoxyphenyl)furo[2,3-d]pyrimidin-4-amine (12)

Using the general procedure described above, compound 12 (61%) was obtained as a light brown solid: mp 100.7-100.8° C.; $R_f$ 0.7 (AcOEt/Hexane, 1:3); $^1$H NMR (DMSO-d6) δ 0.99-1.03 (t, 3H, J=5.6 Hz, OCH$_2$CH$_2$CH$_3$), 1.75-1.79 (m, 2H, J=5.6 Hz, OCH$_2$CH$_2$CH$_3$), 2.17 (s, 3H, CH$_3$), 2.48 (s, 3H, CH$_3$), 3.45 (s, 3H, NCH$_3$), 3.99-4.02 (t, 2H, J=5.6 Hz, OCH$_2$CH$_2$CH$_3$), 4.62 (s, 1H, 5-CH), 7.05-7.07 (d, 2H, J=7.2 Hz, C$_6$H$_4$), 7.27-7.28 (d, 2H, J=7.2 Hz, C$_6$H$_4$); Anal. C$_{18}$H$_{21}$N$_3$O$_2$.

4-(5-methoxyindolin-1-yl)-2,6-dimethylfuro[2,3-d]pyrimidine (8)

To a 100 mL round-bottomed flask, flushed with nitrogen, were added 17 (91 mg, 0.5 mmol), 5-methoxyindoline (82 mg, 0.55 mmol), BuOH (10 mL), and 2-3 drops of conc. HCl. The reaction mixture was heated at reflux with stirring for 12 h until the starting material 17 disappeared (TLC). The reaction solution was allowed to cool to room temperature; the solvent was removed under reduced pressure, and the residue was purified by column chromatography on silica gel with hexane: acetyl acetate=20:1 as the eluent. Fractions containing the product (TLC) were combined and evaporated to afford 93 mg (63%) 8 as a white powder: mp 201.1-202.3° C.; $R_f$ 0.5 (AcOEt/Hexane 3:1); $^1$H NMR (DMSO-$d_6$) δ 2.42 (s, 3H), 2.53 (s, 3H), 3.25 (t, 2H), 3.75 (s, 3H), 4.39 (t, 2H), 6.79 (t, 2H), 6.89 (d, 1H), 8.48 (d, 1H), Anal. $C_{17}H_{17}N_3O_2$ 4-(5-methoxy-1H-indol-1-yl)-2,6-dimethylfuro[2,3-d]pyrimidine (9)

To a solution of 5-methoxy-1H-indole (74 mg, 0.5 mmol) in 5 mL DMF was added NaH (13 mg, 0.55 mmol). The resulting suspension was cooled to 0° C. and stirred for 30 min. To the solution was added 17 (273 mg, 1.5 mmol), and the mixture was stirred for another 2 h at ambient temperature. After adding 1 mL 1 N HCl to terminate the reaction, the solvent was removed under reduced pressure. The crude mixture was purified by silica gel column chromatography using hexane:acetyl acetate=20:1 as the eluent. Fractions containing the product (TLC) were combined and evaporated to afford 66 mg (41%) 9 as colorless crystals: mp 131.6-133.2° C.; $R_f$ 0.28 (AcOEt/Hexane 3:1); $^1$H NMR (DMSO-$d_6$) δ 2.51 (s, 3H), 2.71 (s, 3H), 3.81 (s, 3H), 6.84 (d, 1H, J=2.8 Hz), 6.95 (dd, 1H, $J_1$=7.2 Hz, $J_2$=2.0 Hz), 7.09 (s, 1H), 7.20 (d, 1H, J=2.0 Hz), 8.04 (d, 1H, J=2.8 Hz), 8.57 (d, 1H, J=7.2 Hz), Anal. $C_{17}H_{15}N_3O_2$.

4-(6-methoxy-3,4-dihydroquinolin-1(2H)-yl)-2,6-dimethylfuro[2,3-d]pyrimidine (10)

To a 100 mL round-bottomed flask, flushed with nitrogen were added 17 (91 mg, 0.5 mmol), 6-methoxy-1,2,3,4-tetrahydroquinoline (90 mg, 0.55 mmol), BuOH (10 mL), and 2-3 drops of conc. HCl. The reaction mixture was heated at reflux with stirring for 12 h until the starting material 17 disappeared (TLC). The reaction solution was allowed to cool to room temperature; the solvent was removed under reduced pressure, and the residue was purified by column chromatography on silica gel with hexane:acetyl acetate=20:1 as the eluent. Fractions containing the product (TLC) were combined and evaporated to afford 74 mg (48%) of 10 as a pink powder: mp 108.9-109.6° C.; $R_f$ 0.5 (AcOEt/Hexane 3:1); $^1$H NMR (DMSO-$d_6$) δ 1.90 (m, 2H), 2.28 (s, 3H), 2.48 (s, 3H), 2.73 (t, 2H), 3.75 (s, 3H), 3.94 (t, 2H), 5.53 (s, 1H), 6.76 (dd, 1H, $J_1$=7.2 Hz, $J_2$=2.0 Hz), 6.85 (d, 1H, J=2.0 Hz), 6.05 (d, 1H, J=7.2 Hz), Anal. $C_{18}H_{19}N_3O_2$.

Molecular Modeling

The X-ray crystal structures of tubulin co-crystallized with N-deacetyl-N-(2-mercaptoacetyl) colchicine (DAMA colchicine), a close structural analogue of colchicine (PDB: 1SAO[25], 3.58 Å resolution) and VEGFR-2 co-crystallized with a furo[2,3-d]pyrimidine inhibitor (PDB: 1YWN,[26] 1.71 Å resolution) were obtained from the protein database. The preparation and validation of the PDGFR-□ homology model has been previously reported.[21]

Preparation of Receptor and Ligands for Docking

The crystal structures of tubulin and VEGFR-2 and the homology model for PDGFR-□ were imported into MOE 2013.08.[36] After addition of hydrogen atoms, the protein was then "prepared" using the LigX function in MOE 2013.08 which is a collection of procedures that conducts interactive ligand modification and energy minimization in the active site of a flexible receptor. The procedure was performed with the default settings.

Ligands were built using the molecule builder function in MOE, energy minimized to local minima using the MMF94X forcefield to a constant (0.05 kcal/mol). Ligands were docked into the active site of the prepared protein using LeadIT 2.1.6.[28] The docking site was restricted to the active site pocket residues defined as residues within 6.5 Å of the bound crystal structure ligand. Docking was performed using a hybrid (enthalpy and entropy) approach as the placement method. Docked poses were scored using the default threshold (full score contribution threshold of 0.3; no score contribution threshold of 0.7). Clash handling (protein-ligand and intra-ligand were set at default values of 2.9 Å$^3$ and 0.6 respectively. The maximum number of solutions per iteration was set at 300 and the maximum number of solutions per fragment was set at 300. The best docked poses were exported as sdf files and visualized using the software CCP4 mg.[29]

Docking Procedure

Colchicine Site on Tubulin

The A and B subunits of the protein, along with the crystallized ligand, were retained, while the C, D, and E subunits, GTP, GDP, and Mg ions were deleted. After addition of hydrogen atoms, the protein was then 'prepared' using the LigX function in MOE as described above.

To validate the utility of LeadIT 2.1.6 for docking ligands into the active site, DAMA colchicine, the native ligand in the crystal structure (PDB: 1SAO),[25] was built using the molecule builder, energy minimized, and docked into the active site using the above parameters. The best docked pose of DAMA colchicine displayed an rmsd of 1.10 Å compared with the crystal structure pose of DAMA colchicine. LeadIT 2.1.6 was thus validated for our docking studies. Docking studies were performed for 1-12 and the standard compounds using the same settings. Poses from the docking experiment were visualized using MOE and CCP4 mg.

Kinase Docking

After addition of hydrogen atoms, the proteins were then 'prepared' using the LigX function in MOE as described above. To validate the utility of LeadIT 2.1.6 for docking ligands into the active site of the RTKs, the native ligands in the crystal structure (N-{4-[4-amino-6-(4-methoxyphenyl)furo[2,3-d]pyrimidin-5-yl]phenyl}-N'-[2-fluoro-5-(trifluoromethyl)phenyl]urea from PDB 1YWN[26] for VEGFR2, [6,7-Bis(2-methoxy-ethoxy)quinazoline-4-yl]-(3-ethynyl-phenyl)amine from PDB 1M17 for EGFR[27]) were built using the molecule builder, energy minimized using MMFF94x forcefield to a gradient of 0.05 kcal/mol and docked into the active site using the above parameters. The best docked pose of the native ligand displayed an RMSD of 0.9 Å and 0.91 Å respectively compared to the crystal structure poses, thus validating our docking procedure with LeadIT 2.1.6

Systematic Conformational Search Using Sybyl-X 2.1.1

A systematic conformational search was carried out for 1-12 using Sybyl-X 2.1.1[24] by importing the energy minimized conformations of these compounds used for the docking studies. All applicable rotatable bonds (bonds a-d, see FIGS. 3 & 4) were selected for each compound and the search was carried out using 5° increments and the energy of the ensuing poses was recorded. The poses were exported to MOE 2013.08[36] and RMSD calculations with the docked poses were performed in MOE 2013.08[36] using an SVL code (mol_rmsd) obtained from the SVL exchange website.[37]

Biological Evaluation Methods:

Antibodies.

The PY-HRP antibody was from BD Transduction Laboratories (Franklin Lakes, N.J.). Antibodies against EGFR, PDGFR-β, and VEGFR-2 were purchased from Cell Signaling Technology (Danvers, Mass.).

Phosphotyrosine ELISA.

Cells used were tumor cell lines naturally expressing high levels of EGFR (A431), VEGFR-2 (U251), and PDGFR-β

(SH-SYSY). Expression levels at the RNA level were derived from the NCI Developmental Therapeutics Program (NCI-DTP) web site public molecular target information. Briefly, cells at 60-75% confluence were placed in serum-free medium for 18 h to reduce the background of phosphorylation. Cells were always >98% viable by Trypan blue exclusion. Cells were then pretreated for 60 min with a dose-response relation of 10,000-0.17 nM compound followed in ⅓ Log increments by 100 ng/mL EGF, VEGF, or PDGF-BB for 10 min. The reaction was stopped and cells were permeabilized by quickly removing the media from the cells and adding ice-cold Tris-buffered saline (TBS) containing 0.05% Triton X-100, protease inhibitor cocktail and tyrosine phosphatase inhibitor cocktail. The TBS solution was then removed and cells fixed to the plate for 30 min at 60° C. and further incubation in 70% ethanol for an additional 30 min. Cells were further exposed to block (TBS with 1% BSA) for 1 h, washed, and then a horseradish peroxidase (HRP)-conjugated phosphotyrosine (PY) antibody was added overnight. The antibody was removed, cells were washed again in TBS, exposed to an enhanced luminol ELISA substrate (Pierce Chemical EMD, Rockford, Ill.) and light emission was measured using a Biotek (Winooski, Vt.) microplate reader Data were graphed as a percent of cells receiving growth factor alone and $IC_{50}$ values were calculated from two to three separate experiments (n=8-24) using non-linear regression dose-response relation analysis with Prism 6.0 software (GraphPad, San Diego Calif.).

Chorioallantoic Membrane Assay of Angiogenesis.

The CAM assay is a standard assay for testing antiangiogenic agents. The CAM assay used in these studies was performed as published previously.[22] Briefly, fertile leghorn chicken eggs (Ideal Poultry, Cameron, Tex.) were allowed to grow until 10 days of incubation. The proangiogenic factors, human VEGF-165 and bFGF (100 ng each) were then added at saturation to a 6 mm microbial testing disk (BBL, Cockeysville, Md.) and placed onto the CAM by breaking a small hole in the superior surface of the egg. Antiangiogenic compounds were added 8 h (hour) after the VEGF/bFGF at saturation to the same microbial testing disk and embryos allowed to incubate for an additional 40 h. After 48 h, the CAMs were perfused with 4% paraformaldehyde containing 0.025% Triton X-100 for 20 sec (seconds), excised around the area of treatment, fixed again in 4% paraformaldehyde for 30 min (minutes), placed on Petri dishes, and a digitized image was taken using a dissecting microscope (Wild M400; Bannockburn, Ill.) at 7.5× and SPOT enhanced digital imaging system (Diagnostic Instruments, Sterling Heights, Mich.). A grid was then added to the digital CAM images and the average number of vessels within 5-7 grids counted as a measure of vascularity. Sunitinib and semaxanib were used as positive controls for antiangiogenic activity. Data were graphed as a percent of CAMs receiving bFGF/VEGF only and $IC_{50}$ values calculated from two to three separate experiments (n=5-11) using non-linear regression dose-response relation analysis.

Evaluation of Microtubule Effects

Evaluation of microtubule inhibition was performed using previously described methods.[22] Indirect immunofluorescence was used to evaluate the effects of the compounds on cellular microtubules as described previously.[38] Briefly, A-10 cells were treated for 18 h with vehicle (DMSO) or a compound, and microtubule effects were evaluated microscopically using β-tubulin antibody. The $EC_{50}$ was calculated from 3 independent experiments and expressed as the mean±SD.

Antiproliferative Effects

The antiproliferative effects of compounds were evaluated using the sulforhodamine B (SRB) assay as described previously.[38] The cells were treated with the compounds, vehicle (DMSO) or positive controls, (paclitaxel, CA-4) for 48 h. The $IC_{50}$ values represent the mean of 3 independent experiments each conducted with triplicate wells±SD.

Elemental Analysis

| | | Calcd, % | | | Found, % | | |
|---|---|---|---|---|---|---|---|
| Compd | Formula | C | H | N | C | H | N |
| 2 | $C_{17}H_{19}N_3O$ | 65.16 | 6.11 | 13.41 | 65.20 | 6.16 | 13.21 |
| 3 | $C_{17}H_{19}N_3O_3$ | 65.16 | 6.11 | 13.41 | 65.11 | 6.23 | 13.17 |
| 4 | $C_{18}H_{21}N_3O_4$ | 62.96 | 6.16 | 12.24 | 63.18 | 6.16 | 12.14 |
| 5 | $C_{16}H_{15}N_3O_3$ | 69.64 | 5.09 | 14.13 | 64.63 | 4.98 | 14.14 |
| 6 | $C_{17}H_{17}N_3O_2$ | 69.14 | 5.80 | 14.23 | 68.97 | 5.88 | 14.12 |
| 7 | $C_{17}H_{15}N_3O_2$ | 69.61 | 5.15 | 14.33 | 69.54 | 5.17 | 14.21 |
| 8 | $C_{17}H_{17}N_3O_2$ | 69.14 | 5.80 | 14.23 | 69.17 | 5.78 | 14.22 |
| 9 | $C_{17}H_{15}N_3O_2$ | 69.61 | 5.15 | 14.33 | 69.62 | 5.15 | 14.35 |
| 10 | $C_{18}H_{19}N_3O_2$ | 69.88 | 6.19 | 13.58 | 69.85 | 6.21 | 13.56 |
| 11 | $C_{17}H_{19}N_3O_2$ | 68.67 | 6.44 | 14.13 | 68.89 | 6.48 | 14.06 |
| 12 | $C_{18}H_{21}N_3O_2$ | 69.43 | 6.80 | 13.49 | 69.42 | 6.82 | 13.43 |
| 18 | $C_{16}H_{17}N_3O_3$ | 64.20 | 5.72 | 14.04 | 64.57 | 5.85 | 13.76 |
| 19 | $C_{16}H_{17}N_3O_3 \cdot H_2O$ | 60.56 | 6.03 | 13.24 | 60.67 | 6.15 | 13.03 |
| 20 | $C_{17}H_{19}N_3O_4 \cdot 0.2H_2O$ | 61.32 | 5.87 | 12.62 | 16.41 | 5.94 | 12.30 |
| 21 | $C_{15}H_{13}N_3O_2$ | 63.60 | 4.63 | 14.83 | 63.54 | 4.56 | 14.90 |
| 22 | $C_{16}H_{15}N_3O_2$ | 68.31 | 5.37 | 14.94 | 68.39 | 5.78 | 14.01 |
| 23 | $C_{16}H_{13}N_3O_2$ | 68.81 | 4.69 | 15.05 | 68.84 | 4.77 | 14.96 |
| 24 | $C_{16}H_{17}N_3O_2$ | 67.83 | 6.05 | 14.83 | 67.81 | 6.08 | 14.71 |
| 25 | $C_{17}H_{19}N_3O_2$ | 68.67 | 6.44 | 14.13 | 68.52 | 6.53 | 14.06 |

Those persons skilled in the art will understand that the present invention provides a series of twelve conformationally restricted 4-substituted 2,6-dimethylfuro[2,3-d]pyrimidines and that the bioactive conformation that is required for dual inhibition of microtubule assembly and receptor tyrosine kinases (RTKs) is disclosed herein. All three rotatable single bonds in the comparative compound 1 were sequentially restricted. Compounds 2, 3, 7 and 10 of the present invention showed microtubule depolymerizing activity comparable to or better than compound 1, some with nanomolar $EC_{50}$ values. While compound 8 had no effect on microtubules, both compounds 8 and 10 showed potent RTK inhibition with nanomolar $IC_{50}$s. These compounds confirm that the bioactive conformation for RTK inhibition is different from that for tubulin inhibition. The tetrahydroquinoline compound 10 of the present invention showed the most potent dual tubulin and RTK inhibitory activities (low nanomolar inhibition of EGFR, VEGFR2 and PDGFR-β. Compound 10 has potent activity against cancer cells, overcomes multiple mechanisms of drug resistance.

REFERENCES

1. Folkman, J. Anti-Angiogenesis: New Concept for Therapy of Solid Tumors. *Ann. Surg.* 1972, 175, 409-416.
2. Hanahan, D.; Folkman, J. Patterns and Emerging Mechanisms of the Angiogenic Switch during Tumorigenesis. *Cell* 1996, 86, 353-364.
3. Kerbel, R.; Folkman, J. Clinical translation of angiogenesis inhibitors. *Nat Rev Cancer* 2002, 2, 727-739.
4. Ferrara, N.; Kerbel, R. S. Angiogenesis as a therapeutic target. *Nature* 2005, 438, 967-974.
5. Carmeliet, P.; Jain, R. K. Molecular mechanisms and clinical applications of angiogenesis. *Nature* 2011, 473, 298-307.
6. Jain, R. K.; Carmeliet, P. SnapShot: Tumor Angiogenesis. *Cell* 2012, 149, 1408-1408.e1.
7. Leonard, G. D.; Fojo, T.; Bates, S. E. The Role of ABC Transporters in Clinical Practice. *The Oncologist* 2003, 8, 411-424.
8. Dumontet, C.; Jordan, M. A. Microtubule-binding agents: a dynamic field of cancer therapeutics. *Nat Rev Drug Discov* 2010, 9, 790-803.
9. Lee, J. F. H., L. N. Antimicrotubule Agents. In *Cancer: Principles & Practice of Oncology*, 8th ed.; DeVita, V. T., Jr.; Lawrence, T. S.; Rosenberg, S. A, Ed. Lippincott Williams & Wilkins: Philadelphia, Pa., 2008; p 447-456.
10. Field, J. J.; Waight, A. B.; Senter, P. D. A previously undescribed tubulin binder. *Proc. Natl Acad. Sci.* 2014, 111, 13684-13685.
11. Nathan, P.; Zweifel, M.; Padhani, A. R.; Koh, D.-M.; Ng, M.; Collins, D. J.; Harris, A.; Carden, C.; Smythe, J.; Fisher, N.; Taylor, N. J.; Stirling, J. J.; Lu, S.-P.; Leach, M. O.; Rustin, G. J. S.; Judson, I. Phase I Trial of Combretastatin A4 Phosphate (CA4P) in Combination with Bevacizumab in Patients with Advanced Cancer. *Clin. Cancer Res.* 2012, 18, 3428-3439.
12. Patterson, D. M.; Zweifel, M.; Middleton, M. R.; Price, P. M.; Folkes, L. K.; Stratford, M. R. L.; Ross, P.; Halford, S.; Peters, J.; Balkissoon, J.; Chaplin, D. J.; Padhani, A. R.; Rustin, G. J. S. Phase I Clinical and Pharmacokinetic Evaluation of the Vascular-Disrupting Agent OXi4503 in Patients with Advanced Solid Tumors. *Clin. Cancer Res.* 2012, 18, 1415-1425.
13. Kavallaris, M. Microtubules and resistance to tubulin-binding agents. *Nat Rev Cancer* 2010, 10, 194-204.
14. Cesca, M.; Bizzaro, F.; Zucchetti, M.; Giavazzi, R. Tumor delivery of chemotherapy combined with inhibitors of angiogenesis and vascular targeting agents. *Front Oncol* 2013, 3, 259.
15. Hall, M.; Gourley, C.; McNeish, I.; Ledermann, J.; Gore, M.; Jayson, G.; Perren, T.; Rustin, G.; Kaye, S. Targeted anti-vascular therapies for ovarian cancer: current evidence. *Br J Cancer* 2013, 108, 250-258.
16. Heath, V. L.; Bicknell, R. Anticancer strategies involving the vasculature. *Nat Rev Clin Oncol* 2009, 6, 395-404.
17. Holohan, C.; Van Schaeybroeck, S.; Longley, D. B.; Johnston, P. G. Cancer drug resistance: an evolving paradigm. *Nat Rev Cancer* 2013, 13, 714-726.
18. Ma, J.; Waxman, D. J. Combination of antiangiogenesis with chemotherapy for more effective cancer treatment. *Mol Cancer Ther* 2008, 7, 3670-3684.
19. Matthews, D. J. G., M. E. Current Challenges and Future Directions. In *Targeting Protein Kinases for Cancer Therapy*, Matthews, D. J. G., M. E., Ed. Wiley & Sons Inc: Hoboken, N.J., 2010; pp 623-663.
20. Postel-Vinay, S.; Armand, J.-P. Targeting Angiogenesis. In *Targeted Therapies in Oncology*, 2nd ed.; Giaccone, G.; Soria, J.-C., Eds. CRC Press: Boca Raton, Fla., 2013; pp 283-314.
21. Gangjee, A.; Zaware, N.; Raghavan, S.; Ihnat, M.; Shenoy, S.; Kisliuk, R. L. Single Agents with Designed Combination Chemotherapy Potential: Synthesis and Evaluation of Substituted Pyrimido[4,5-b]indoles as Receptor Tyrosine Kinase and Thymidylate Synthase Inhibitors and as Antitumor Agents. *J Med Chem* 2010, 53, 1563-1578.
22. Zhang, X.; Raghavan, S.; Ihnat, M.; Thorpe, J. E.; Disch, B. C.; Bastian, A.; Bailey-Downs, L. C.; Dybdal-Hargreaves, N. F.; Rohena, C. C.; Hamel, E.; Mooberry, S. L.; Gangjee, A. The design and discovery of water soluble 4-substituted-2,6-dimethylfuro[2,3-d]pyrimidines as multitargeted receptor tyrosine kinase inhibitors and microtubule targeting antitumor agents. *Bioorg Med Chem* 2014, 22, 3753-3772.
23. Anighoro, A.; Bajorath, J.; Rastelli, G. Polypharmacology: Challenges and Opportunities in Drug Discovery. *J. Med. Chem.* 2014, 57, 7874-7887.
24. Certera, L. P., 210 N. Tucker Blvd, Suite 350, St. Louis Mo. 63101. www.certara.com. *Sybyl X* 2.1.1, 2013.
25. Ravelli, R. B. G.; Gigant, B.; Curmi, P. A.; Jourdain, I.; Lachkar, S.; Sobel, A.; Knossow, M. Insight into tubulin regulation from a complex with colchicine and a stathmin-like domain. *Nature* 2004, 428, 198-202.
26. Miyazaki, Y; Matsunaga, S.; Tang, J.; Maeda, Y.; Nakano, M.; Philippe, R. J.; Shibahara, M.; Liu, W.; Sato, H.; Wang, L.; Nolte, R. T. Novel 4-amino-furo[2,3-d]pyrimidines as Tie-2 and VEGFR2 dual inhibitors. *Bioorg Med Chem Lett.* 2005, 15, 2203-2207.
27. Stamos, J.; Sliwkowski, M. X.; Eigenbrot, C. Structure of the epidermal growth factor receptor kinase domain alone and in complex with a 4-anilinoquinazoline inhibitor. *J Biol Chem* 2002, 277, 46265-46272.
28. *LeadIT* 2.1.6 BioSolveIT GmbH, An der Ziegelei 79, 53757 St. Augustin, Germany.
29. McNicholas, S.; Potterton, E.; Wilson, K. S.; Noble, M. E. M. Presenting your structures: the CCP4 mg molecular-graphics software. *Acta Crystallogr Sec D* 2011, 67, 386-394.
30. Kornev, A. P.; Haste, N. M.; Taylor, S. S.; Ten Eyck, L. F. Surface comparison of active and inactive protein kinases identifies a conserved activation mechanism. *Proc Natl Acad Sci* 2006, 103, 17783-17788.
31. Gangjee, A.; Yu, J.; Copper, J. E.; Smith, C. D. Discovery of novel antitumor antimitotic agents that also reverse tumor resistance. *J Med Chem* 2007, 50, 3290-301.
32. Zhang, X.; Zhou, X.; Kisliuk, R. L.; Piraino, J.; Cody, V; Gangjee, A. Design, synthesis, biological evaluation and X-ray crystal structure of novel classical 6,5,6-tricyclic benzo[4,5]thieno[2,3-d]pyrimidines as dual thymidylate synthase and dihydrofolate reductase inhibitors. *Bioorg Med Chem* 2011, 19, 3585-94.
33. Rosowsky, A.; Chen, K. K.; Lin, M. 2,4-Diaminothieno[2,3-d]pyrimidines as antifolates and antimalarials. 3. Synthesis of 5,6-disubstituted derivatives and related tetracyclic analogs. *J Med Chem* 1973, 16, 191-4.

34. Wartenberg, F. H. K., T.; Wetzel, W.; Wydra, M.; Benz, A. Method for Producing Benzo Annelated Heterocycles. PCT Int. Appl. (2001), CODEN: PIXXD2 WO 01/77099 A1 19980305.
35. Yadav, P. P.; Gupta, P.; Chaturvedi, A. K.; Shukla, P. K.; Maurya, R. Synthesis of 4-hydroxy-1-methylindole and benzo[b]thiophen-4-ol based unnatural flavonoids as new class of antimicrobial agents. *Bioorg Med Chem* 2005, 13, 1497-1505.
36. *Molecular Operating Environment (MOE)*, 2013.08, Chemical Computing Group Inc., 1010 Sherbooke St. West, Suite #910, Montreal, QC, Canada, H3A 2R7: 2014.
37. *mol_rmsd, Scientific Vector Language (SVL) source code provided* by Chemical Computing Group Inc., 1010 Sherbooke St. West, Suite #910, Montreal, QC, Canada, H3A 2R7, 2013.
38. Risinger, A. L.; Jackson, E. M.; Polin, L. A.; Helms, G. L.; LeBoeuf, D. A.; Joe, P. A.; Hopper-Borge, E.; Ludueña, R. F.; Kruh, G. D.; Mooberry, S. L. The Taccalonolides: Microtubule Stabilizers That Circumvent Clinically Relevant Taxane Resistance Mechanisms. *Cancer Res* 2008, 68, 8881-8888.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A compound of Formula II, or a pharmaceutically acceptable salt thereof:

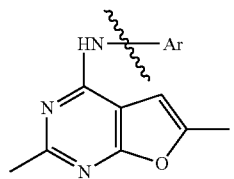

II wherein Ar is selected from the group consisting of:

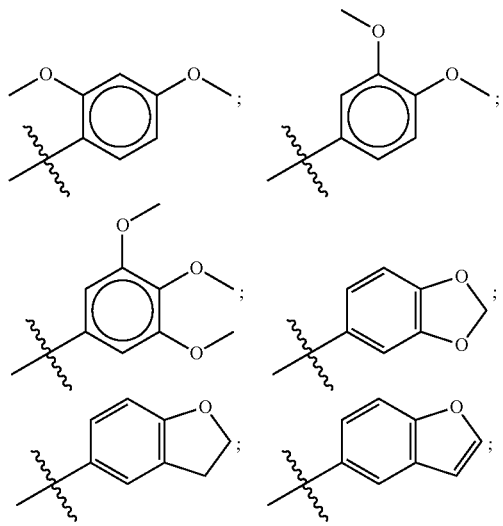

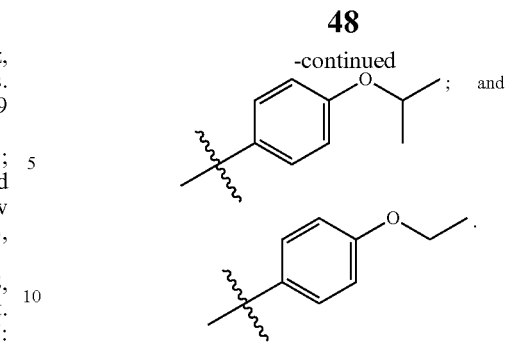

2. A method of treating a patient having cancer comprising administering to said patient a therapeutically effective amount of at least one compound of Formula II, or a pharmaceutically acceptable salt thereof:

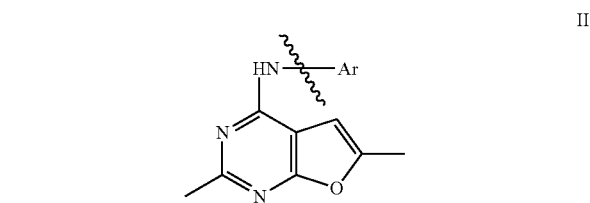

II wherein Ar is selected from the group consisting of:

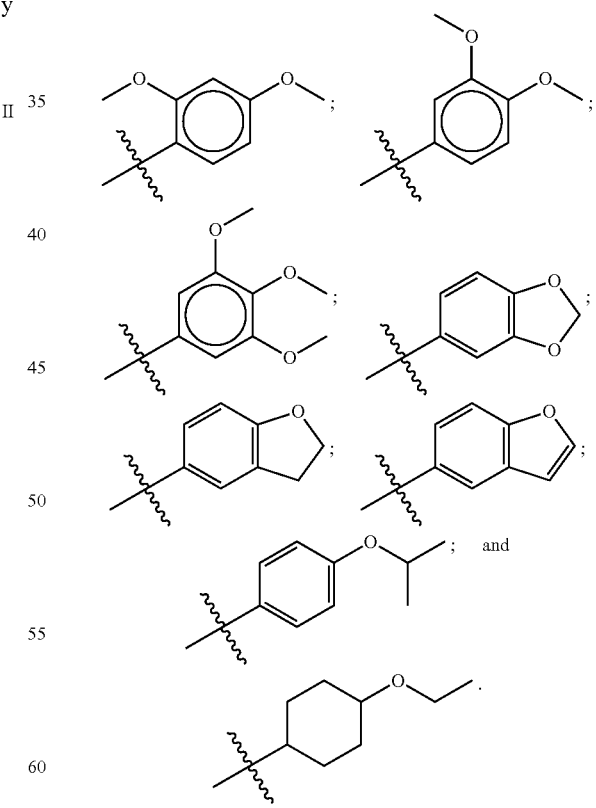

and optionally a pharmaceutical acceptable carrier, excipient or adjuvant.

3. A method of treating a patient having cancer comprising administering to said patient a therapeutically effective amount of at least one compound of Formula I, or a pharmaceutically acceptable salt thereof:
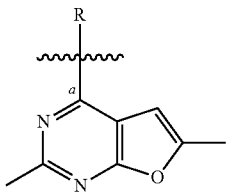
wherein R is selected from the group consisting of:
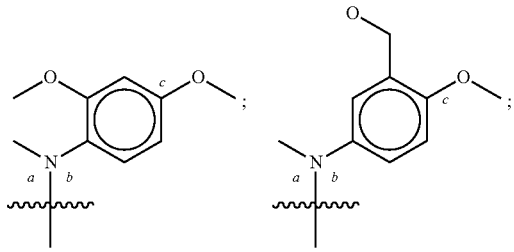
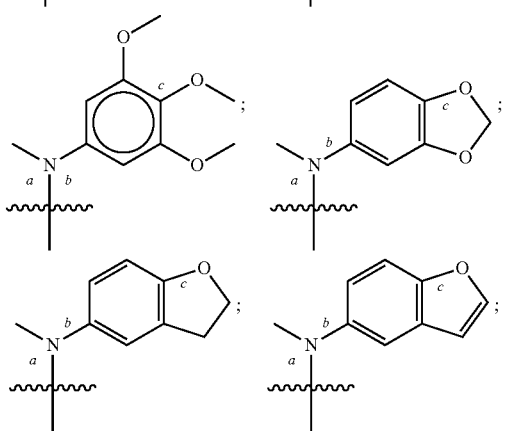
-continued
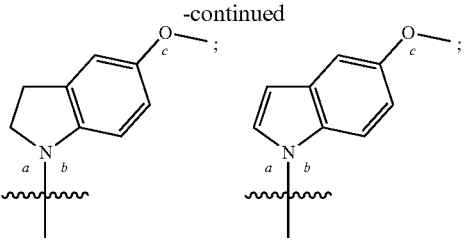
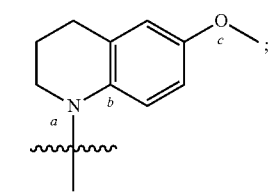
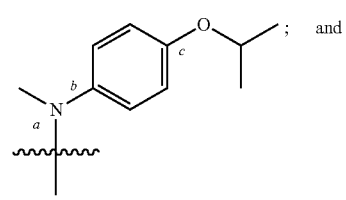; and
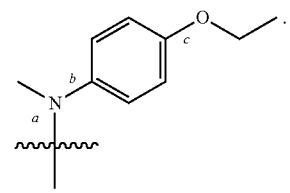
and optionally a pharmaceutical acceptable carrier, excipient or adjuvant.
* * * * *